United States Patent
Tolmie et al.

(10) Patent No.: US 9,974,910 B2
(45) Date of Patent: May 22, 2018

(54) SYSTEMS AND METHODS FOR COMPENSATING LONG TERM SENSITIVITY DRIFT OF ELECTROCHEMICAL GAS SENSORS EXPOSED TO NITRIC OXIDE

(71) Applicant: Mallinckrodt Hospital Products IP Limited, Dublin (IE)

(72) Inventors: Craig R. Tolmie, Stoughton, WI (US); Jeff Milsap, Cambridge, WI (US); Jaron M. Acker, Madison, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 0 days. days.

(21) Appl. No.: 15/281,176

(22) Filed: Sep. 30, 2016

(65) Prior Publication Data
US 2017/0014592 A1    Jan. 19, 2017

Related U.S. Application Data

(63) Continuation of application No. 15/010,999, filed on Jan. 29, 2016, which is a continuation of application
(Continued)

(51) Int. Cl.
*A61M 16/00*    (2006.01)
*G01N 33/00*    (2006.01)
(Continued)

(52) U.S. Cl.
CPC .... *A61M 16/0051* (2013.01); *A61M 16/0003* (2014.02); *A61M 16/085* (2014.02); *A61M 16/1005* (2014.02); *A61M 16/12* (2013.01); *A61M 16/201* (2014.02); *G01N 27/4163* (2013.01); *G01N 33/0006* (2013.01); *G01N 33/0008* (2013.01); *G01N 33/0037* (2013.01); *A61M 16/16* (2013.01); *A61M 2016/102* (2013.01); *A61M 2016/1035* (2013.01); *A61M 2202/0275* (2013.01); *A61M 2205/18* (2013.01);
(Continued)

(58) Field of Classification Search
CPC ............ A61M 16/1005; A61M 16/201; A61M 16/0051; G01N 27/4163; G01N 33/0006; G01N 33/0037
See application file for complete search history.

(56) References Cited

U.S. PATENT DOCUMENTS

| 4,553,423 A | 11/1985 | Tanimoto |
| 5,129,401 A | 7/1992 | Corenman et al. |

(Continued)

*Primary Examiner* — Tam-Uyen (Jackie) T Ho
*Assistant Examiner* — Jonathan Paciorek

(57) ABSTRACT

Described are systems and methods for compensating long term sensitivity drift of catalytic type electrochemical gas sensors used in systems for delivering therapeutic nitric oxide (NO) gas to a patient by compensating for drift that may be specific to the sensors atypical use in systems for delivering therapeutic nitric oxide gas to a patient. The long term sensitivity drift of catalytic type electrochemical gas sensors may be addressed using calibration schedules, which can factor in the absolute change in set dose of NO being delivered to the patient that can drive one or more baseline calibrations. The calibration schedules can be used to reduce the amount of times the sensor goes offline.

20 Claims, 9 Drawing Sheets

Related U.S. Application Data

No. 14/626,409, filed on Feb. 19, 2015, now Pat. No. 9,279,794.

(60) Provisional application No. 61/941,725, filed on Feb. 19, 2014.

(51) Int. Cl.

| | | |
|---|---|---|
| *A61M 16/20* | (2006.01) | |
| *A61M 16/12* | (2006.01) | |
| *A61M 16/10* | (2006.01) | |
| *A61M 16/08* | (2006.01) | |
| *G01N 27/416* | (2006.01) | |
| *A61M 16/16* | (2006.01) | |

(52) U.S. Cl.
CPC ..... *A61M 2205/27* (2013.01); *A61M 2205/33* (2013.01); *A61M 2205/502* (2013.01); *A61M 2205/52* (2013.01); *A61M 2205/581* (2013.01); *A61M 2205/583* (2013.01); *A61M 2205/70* (2013.01); *A61M 2205/702* (2013.01)

(56) References Cited

U.S. PATENT DOCUMENTS

| | | | |
|---|---|---|---|
| 5,526,280 | A | 6/1996 | Consadori et al. |
| 5,558,083 | A | 9/1996 | Bathe et al. |
| 5,732,693 | A | 3/1998 | Bathe et al. |
| 5,752,504 | A | 5/1998 | Bathe et al. |
| 6,948,352 | B2 | 9/2005 | Rabbett et al. |
| 6,955,171 | B1 * | 10/2005 | Figley ............... A61M 16/00 128/204.21 |
| 7,147,761 | B2 | 12/2006 | Davis et al. |
| 7,366,626 | B2 * | 4/2008 | Hazama ............ G01N 27/4175 702/104 |
| 2004/0055359 | A1 | 3/2004 | Ketler et al. |
| 2010/0078026 | A1 * | 4/2010 | Andrieux ........... A61M 16/024 128/204.21 |
| 2010/0292544 | A1 | 11/2010 | Sherman |
| 2011/0220103 | A1 | 9/2011 | Fine et al. |
| 2012/0093948 | A1 * | 4/2012 | Fine .................... A61M 16/10 424/718 |
| 2012/0240927 | A1 * | 9/2012 | Bathe .................. A61M 16/20 128/203.12 |
| 2013/0000643 | A1 | 1/2013 | Bathe et al. |
| 2014/0000596 | A1 | 1/2014 | Acker |
| 2014/0037506 | A1 | 2/2014 | Miki et al. |
| 2014/0127081 | A1 | 5/2014 | Fine et al. |

* cited by examiner

SYSTEMS AND METHODS FOR COMPENSATING LONG TERM SENSITIVITY DRIFT OF ELECTROCHEMICAL GAS SENSORS EXPOSED TO NITRIC OXIDE

CROSS-REFERENCE TO RELATED APPLICATIONS

This application claims the benefit under 35 U.S.C. § 119(e) to U.S. Provisional Application No. 61/941,725, filed Feb. 19, 2014, the entire contents of which are incorporated herein by reference in their entirety.

FIELD

The present invention generally relates to systems and methods for compensating long term sensitivity drift of electrochemical gas sensors exposed to nitric oxide, for example, in a controlled environment.

BACKGROUND

There exist many variations of electrochemical sensors which, although they may appear similar, function vastly differently. For example, some electrochemical sensors can be used for detection of the presence of a specific gas while others detect concentrations of a specific gas. Even further some electrochemical sensors function with liquids and do not function with gases. Focusing on electrochemical gas sensors, some of these gas sensors use galvanic reactions while others use catalytic reactions. Further, some of these gas sensors need electricity to function while others do not need electricity and in some instances these sensors actually generate electricity. Even further, within similar types of electrochemical gas sensors that have the same electrical requirements, this small subset of sensors can have a vast amount of variation depending on the function of the cell and/or the gas which the cell reacts with.

Focusing on catalytic type electrochemical gas sensors, these sensors are typically used as toxic gas sensors. When used as toxic gas sensors (e.g., for monitoring of smoke stacks emissions) these sensors may only be exposed to the toxic gas for short durations of time or intermittent duty times and/or they may only be used to detect significantly low concentrations of a gas (e.g., gas in the parts per billion (PPB) range). However, unlike the way these sensors are used as toxic gas sensors, systems for delivering therapeutic nitric oxide gas to a patient can use catalytic type electrochemical gas sensors to confirm accurate dosing of therapeutic gas such as inhaled nitric oxide (NO). These delivery systems, that include catalytic type electrochemical gas sensors, can be used to deliver therapeutic nitric oxide to a patient at a dosage in the parts per million (e.g., 1 PPM to 80 PPM, 0.1 PPM to 80 PPM, etc.) for a prolonged period of time (e.g., many hours, days, weeks, months, etc.) under continuous gas monitoring.

Generally speaking, this type of use of catalytic type electrochemical gas sensors in systems for delivering therapeutic nitric oxide gas to a patient is considered to be atypical and may present problems not seen when using these sensors in a more conventional manner (e.g., typical toxic gas sensor applications). These issues, can be important as users (e.g., doctors, nurses, etc.) may confirm dosing of the therapeutic drug based on the output of these sensors.

Accordingly, a need exists to overcome these issues for at least ensuring proper confirmation of dosing.

SUMMARY

There are several ways to address the above problems, including for example performing recalibrations of the sensor over particular time intervals, providing messages and/or indicators that warn a user of operating conditions and performance of calibrations, use of dual sensors to measure the amount of the target gas in a breathing circuit, and detecting if sensor output is beyond a threshold range.

Principles and embodiments relate generally to a method for compensating for output drift of an electrochemical gas sensor exposed to nitric oxide in a controlled environment, comprising identifying a time for executing a calibration from a sensor recalibration schedule stored in a system controller memory, and detecting if an alarm is active or has been active within a predetermined timeframe at the time the calibration is to be executed, wherein the calibration is postponed if the active alarm is detected or has been detected within the predetermined timeframe, and execute the calibration if the active alarm is not detected or has not been detected within the predetermined timeframe.

Embodiments also relate to establishing a dosage of a target gas to be delivered to a breathing circuit indicated by a setting in a system controller, identifying a change in the setting in the system controller, calculating the magnitude of a change in the dosage of the target gas to be delivered to the breathing circuit, identifying the sensor recalibration schedule stored in the system controller memory that is specified for the magnitude of the change in the dosage of the target gas, and implementing the sensor recalibration schedule identified.

Embodiments also relate to continuously measuring a concentration of the target gas in the breathing circuit with a first sensor, communicating a signal representative of the target gas concentration from the first sensor to the system controller over a communication path, and determining a response by the first sensor to the change in concentration of the target gas.

Embodiments also relate to interrupting the continuous measuring of the target gas concentration when indicated by the identified sensor recalibration schedule, exposing the first sensor to a gas having a zero concentration of the target gas for a period of time sufficient to detect the output value indicative of the zero concentration, and determining the response by the first sensor to the gas having a zero concentration of the target gas.

Embodiments also relate to a sensor recalibration schedule comprises a set of values representing intended intervals between interruptions of the continuous measuring of the target gas concentration.

Embodiments also relate to an intended intervals are larger for a smaller change in the setting in the system controller.

Embodiments also relate to storing the response of the first sensor to the gas having a zero concentration of the target gas in the system controller memory.

Embodiments also relate to accessing a slope of a previous calibration line stored in the system controller memory, and generating a new calibration line using the stored response of the first sensor to the gas having the zero concentration of the target gas and the slope of the previous calibration line.

Embodiments also relate to identifying the type of first sensor continuously measuring a concentration of the target gas in the breathing circuit, storing the type of first sensor in the system controller, and utilizing the type of first sensor in identifying the sensor recalibration schedule.

Embodiments also relate to a first sensor that is a three terminal electrochemical nitric oxide gas sensor or a four terminal electrochemical nitric oxide gas sensor.

Embodiments also relate to selecting a source of ambient air to flow to the first sensor when interrupting the continuous measuring of the target gas concentration in the breathing circuit without disconnecting a sample line from an inspiratory side of the patient breathing circuit.

Embodiments also relate to switching a valve connected to and in fluid communication with the patient breathing circuit to allow ambient air to flow to the first sensor when interrupting the continuous measuring of the target gas concentration in the breathing circuit without disconnecting a sample line from an inspiratory side of the patient breathing circuit.

Embodiments also relate to verifying the valve has switched to allow ambient air to flow to the sensor.

Embodiments also relate to postponing execution of the calibration by a predetermined time period, and detecting if an alarm is active or has been active within a predetermined timeframe after the predetermined time period has elapsed, wherein the calibration is postponed if the active alarm is detected or has been detected within a predetermined timeframe, and executed the calibration if the active alarm is not detected or has been detected within a predetermined timeframe.

Embodiments also relate to (i) detecting the presence of interfering gas, and postponing execution of the calibration by a predetermined time period if interfering gas is detected and/or (ii) detecting if a user is interacting or has interacted with the therapeutic gas delivery system within a predetermined timeframe at the time the calibration is to be executed.

Embodiments also relate to displaying a message to a user when measuring the concentration of the target gas in the breathing circuit with the first sensor is interrupted to execute the calibration.

Embodiments also relate to measuring the concentration of the target gas in the breathing circuit with a second sensor when measuring the concentration of the target gas in the breathing circuit with the first sensor is interrupted, so a measure of the target gas concentration is displayed to a user during recalibration.

Embodiments also relate to exposing the second sensor to the gas having a zero concentration of the target gas for the period of time sufficient to de-saturate and/or detect the output value indicative of the zero concentration after exposing the first sensor to the gas having a zero concentration of the target gas for the period of time sufficient to de-saturate and/or detect the output value indicative of the zero concentration, and comparing the output value from the second sensor to the output value of the first sensor to determine the difference in drift between the first and second sensor.

Principles and embodiments also relate generally to a method for compensating for output drift of an electrochemical gas sensor exposed to nitric oxide in a controlled environment, comprising identifying a time for executing a calibration from a sensor recalibration schedule stored in a system controller memory, detecting if an alarm is active or has been active within a predetermined timeframe at the time the calibration is to be executed, wherein the calibration is postponed if the active alarm is detected or has been detected within the predetermined timeframe, detecting if a user is interacting or has interacted with the therapeutic gas delivery system within a predetermined timeframe at the time the calibration is to be executed, wherein the calibration is postponed if the user is interacting or has interacted with the therapeutic gas delivery system within the predetermined timeframe, detecting if one or more interfering gasses are causing or have caused sensor output to be outside a threshold range within a predetermined timeframe at the time the calibration is to be executed, wherein the calibration is postponed if the sensor output is or has been out of range within the predetermined timeframe at the time the calibration is to be executed, executing the calibration (i) if the active alarm is not detected or has not been detected within the predetermined timeframe, (ii) if the user is not interacting or has not interacted with the therapeutic gas delivery system within the predetermined timeframe, and (iii) if the sensor output is not or has not out of range within a predetermined timeframe.

Principles and embodiments also relate generally to a method for compensating for output drift of an electrochemical gas sensor exposed to nitric oxide in a controlled environment, comprising delivering a therapeutic gas comprising NO to a patient in need thereof, detecting a change in set dose of the therapeutic gas, selecting a sensor recalibration schedule stored in a system controller memory in response to the change in set dose, identifying a time for executing a calibration from the selected sensor recalibration schedule, detecting if an alarm is active or has been active within a predetermined timeframe at the time the calibration is to be executed, wherein the calibration is postponed if the active alarm is detected or has been detected within the predetermined timeframe, detecting if a user is interacting or has interacted with the therapeutic gas delivery system within a predetermined timeframe at the time the calibration is to be executed, wherein the calibration is postponed if the user is interacting or has interacted with the therapeutic gas delivery system within the predetermined timeframe, detecting if one or more interfering gasses are causing or have caused sensor output to be outside a threshold range within a predetermined timeframe at the time the calibration is to be executed, wherein the calibration is postponed if the sensor output is or has been out of range within the predetermined timeframe at the time the calibration is to be executed, executing the calibration (i) if the active alarm is not detected or has not been detected within the predetermined timeframe, (ii) if the user is not interacting or has not interacted with the therapeutic gas delivery system within the predetermined timeframe, and (iii) if the sensor output is not or has not out of range within a predetermined timeframe, and displaying a message to a user, when executing a calibration, indicating that a calibration is in effect and/or recording in an electronic medical record (EMR) the occurrence of a calibration to inform the user of the system's activity.

BRIEF DESCRIPTION OF THE DRAWINGS

The features and advantages of the present invention will be more fully understood with reference to the following, detailed description when taken in conjunction with the accompanying figures, wherein.

DETAILED DESCRIPTION

The present invention generally relates to systems and methods for compensating long term sensitivity drift of electrochemical gas concentration sensors used in a controlled environment such as in systems for delivering therapeutic nitric oxide (NO) gas to a patient. To compensate for long term sensitivity drift of electrochemical gas sensors used in systems delivering therapeutic NO gas to a patient, systems and methods of the present invention, at times, use a calibration process that factors in changes in the set dose of NO being delivered to the patient. Factoring in changes in the set dose of NO being delivered to the patient, the calibration process can initiate a plurality of baseline calibrations of the electrochemical gas sensor where the frequency of the baseline calibrations are, at times, based on the magnitude of the concentration change of the set dose (i.e., the absolute change in concentration from an initial set dose to a final set dose). This can result in compensation of sensitive changes in the electrochemical gas sensor.

This long term sensitivity drift may be specific to the sensors atypical use because, for example, the sensor can be exposed to the substantially high NO concentrations (e.g., an order of magnitude more than seen during typical use) and/or this exposure can be for substantially long durations of time (e.g., several orders of magnitude longer than during typical use) such as when the sensor undergoes continuous duty operation associated with inhaled NO therapy. Additionally, the sensor may be subjected to localized effects such as, but not limited to, temperature changes, chemical changes, humidity, electrolyte conductivity, and/or changes in physical internal resistance, to name a few. Accordingly, systems and methods of the present invention compensate for this long term drift that may be specific to the sensor being used in an atypical manner, for example, using, amongst other things, calibration processes.

Further, systems and method of the present invention can factor in actions occurring at the therapeutic NO gas delivery system and/or aspects of the surrounding environment prior to performing a baseline calibration and, in at least some instances, can respond accordingly. In at least some instances, this can result in postponing of a baseline calibration and/or rejected using the sensor's output for the baseline calibration.

Delivery and Sampling System Overview

Figure 1A:
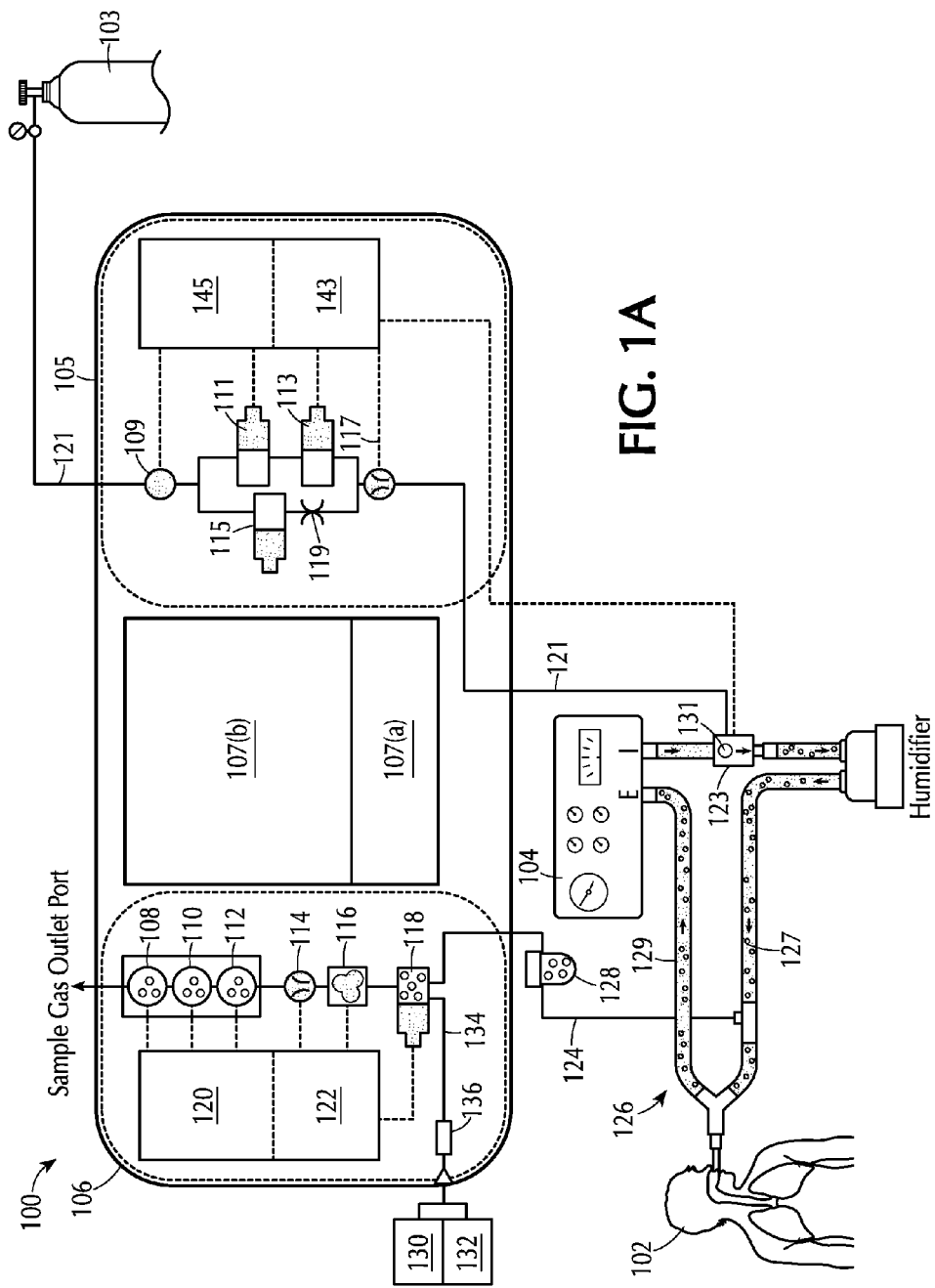
FIGS. 1A-1B illustratively depict exemplary systems, which include exemplary catalytic type electrochemical gas sensors, for delivering therapeutic nitric oxide gas to a patient, in need thereof, in accordance with exemplary embodiments of the present invention.
Figure 1B:
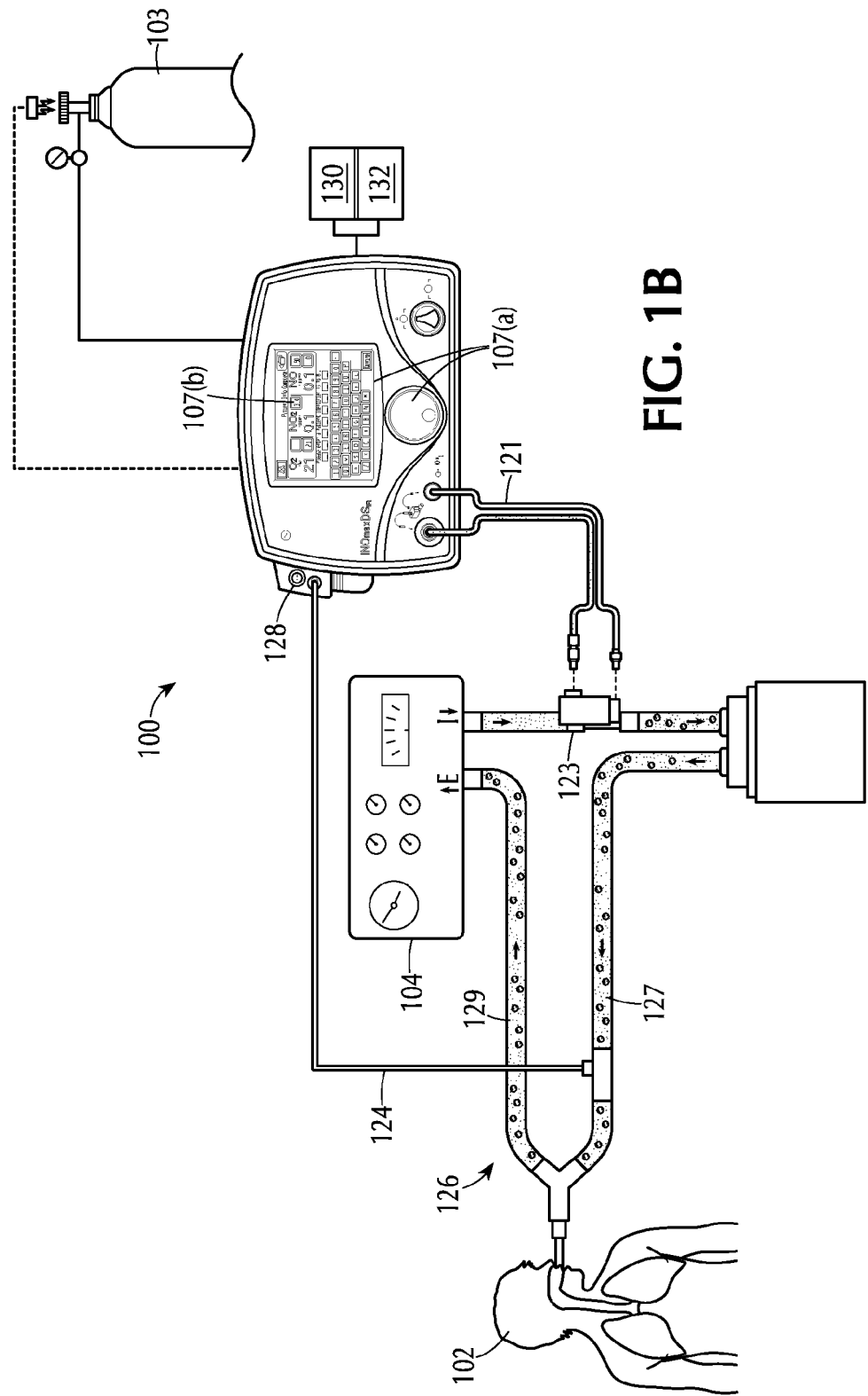

Referring to FIGS. 1A-1B, exemplary therapeutic gas delivery systems (e.g., which include an electrochemical gas sensor), for delivering therapeutic gas to a patient are illustratively depicted. It will be understood that catalytic type electrochemical gas sensors and/or any teachings of the present invention can be used in any applicable system for delivering therapeutic gas to a patient. For example, systems and methods of the present invention can use, modify, and/or be affiliated with the delivery systems and/or other teachings of U.S. Pat. No. 5,558,083 entitled "NO Delivery System" and/or U.S. Pat. No. 5,752,504 entitled "System for Monitoring Therapy During Calibration", the contents of both of which are incorporated herein by reference in their entireties.

The electrochemical gas sensors, systems for delivering therapeutic gas to a patient, and systems and methods are, at times, described as being directed towards NO. For example, the electrochemical gas sensor is, at times, described as a nitric oxide sensor, NO sensor, or the like; the therapeutic gas delivery system is, at times, describes as a therapeutic nitric oxide delivery system, therapeutic NO delivery system, nitric oxide delivery system, NO delivery system, or the like; and/or the therapeutic gas is, at times described as nitric oxide, NO, or the like. This is merely for ease and is in no way meant to be a limitation. Of course the teachings disclosed herein can, when appropriate, be used for other therapeutic gas.

In exemplary embodiments, a therapeutic gas delivery system 100 can be used to deliver therapeutic gas, such as NO, to a patient 102 who may be using an assisted breathing apparatus such as a ventilator 104 or other device used to introduce therapeutic gas to the patient, for example, a nasal cannula, endotracheal tube, face mask, or the like. For ease, systems and methods of the present invention are described, at times, as being for use with a ventilator. This is merely for ease and is in no way meant to be a limitation. Therapeutic gas can be supplied from a therapeutic gas source 103. Therapeutic gas source 103 can be any source of therapeutic gas such as a therapeutic gas contained in a cylinder (e.g., a cylinder containing NO), NO gas generator, or the like. Of course other sources of therapeutic gas can be used.

Therapeutic gas delivery system 100 can include, amongst other things, a gas delivery subsystem(s) 105 and/or a gas sampling system(s) 106. Therapeutic gas delivery system 100 can also include user input interface(s) 107(a) and/or display(s) 107(b), which may be combined, that can include a display and a keyboard and/or buttons, or may be a touchscreen device. User input interface 107(a) and/or display 107(b) can receive desired settings from the user, such as the patient's prescription (in mg/kg ideal body weight, mg/kg/hr, mg/kg/breath, mL/breath, cylinder concentration, delivery concentration or set dose, duration, etc.), the patient's age, height, sex, weight, etc. User input interface 107(a) and/or display 107(b) can in at least some instances be used to confirm that the desired patient dosing (e.g., user input desired dose of NO PPM) using a gas sampling system 106.

It will be understood that any of the elements of system 100 can be combined and/or further separated. For ease elements are, at times, described as being specific to subsystems. This is merely for ease and is in no way meant to be a limitation.

To at least deliver desired set doses of therapeutic gas to a patient and/or sample therapeutic gas being delivered to a patient, therapeutic gas delivery system 100 can include a system controller that may comprise one or more processors and memory, where the system controller may be for example a computer system, a single board computer, one or more application-specific integrated circuits (ASICs), or a combination thereof. Processors can be coupled to memory and may be one or more of readily available memory such as random access memory (RAM), read only memory (ROM), flash memory, compact/optical disc storage, hard disk, or any other form of local or remote digital storage. Support circuits can be coupled to processors, to support processors, sensors, valves, sampling systems, delivery systems, user inputs, displays, injector modules, breathing apparatus, etc. in a conventional manner. These circuits can include cache memory, power supplies, clock circuits, input/output circuitry, analog-to-digital and/or digital-to-analog convertors, subsystems, power controllers, signal conditioners, and the like. Processors and/or memory can be in communication with sensors, valves, sampling systems, delivery systems, user inputs, displays, injector modules, breathing apparatus, etc. Communication to and from the system controller may be over a communication path, where the communication path may be wired or wireless, and wherein suitable hardware, firmware, and/or software may be configured to interconnect components and/or provide electrical communications over the communication path(s).

The clock circuits may be internal to the system controller and/or provide a measure of time relative to an initial start, for example on boot-up. The system may comprise a real-time clock (RTC) that provides actual time, which may be synchronized with a time-keeping source, for example a network. The memory may be configured to receive and store values for calculations and/or comparison to other values, for example from sensor(s), pumps, valves, etc.

In exemplary embodiments, the memory may store a set of machine-executable instructions (or algorithms), when executed by processors, that can cause the sampling system and/or delivery system to perform various methods and operations. For example, the delivery system can perform a method to, for example, deliver a desired set dose of therapeutic gas (e.g., NO concentration, NO PPM, etc.) to a patient in need thereof comprising: receiving and/or determining a desired set dose of therapeutic gas to be delivered to a patient, for example, that may be input by a user; measuring flow in the inspiratory limb of a patient breathing circuit; delivering therapeutic gas containing NO to the patient during inspiratory flow; monitoring inspiratory flow or changes in the inspiratory flow; and varying the quantity (e.g. volume or mass) of therapeutic gas delivered in a subsequent inspiratory flow.

For another example, the sampling system can perform a method to, for example, determine the concentration of target gas (e.g., NO) being delivered to a patient comprising: actuating a sampling pump and/or opening a gas sampling valve (e.g., three way valve, etc.) to obtain a gas sample from the inspiratory limb of a patient breathing circuit, the gas sample being of blended air and therapeutic gas (e.g., NO) being delivered to a patient; exposing the gas sample to gas sensors (e.g., catalytic type electrochemical gas sensors); obtaining information from the sensor indicative of the concentration of target gas (e.g., NO, nitrogen dioxide, oxygen) being delivered to the patient; communicating to the user the concentration of the target gas.

For another example, the sampling system can perform a method to, for example, perform calibrations (e.g., baseline calibrations) of the gas sensor (e.g., catalytic type sensor, electrochemical gas sensor, NO sensor, etc.) comprising: actuating a sampling pump and/or opening a gas sampling valve (e.g., three way valve, etc.) to obtain a gas sample of ambient air (e.g., conditioned room air); exposing the gas sample of ambient air to gas sensors (e.g., catalytic electrochemical NO gas sensors); obtaining information from the sensor indicative of concentration of target gas (e.g., NO) in the ambient air (e.g., 0 PPM NO); and generating a new calibration line and/or modifying an existing calibration line by, for example, replacing the initial and/or previous information indicative of zero concentration target gas (e.g., 0 PPM NO) with the obtained information indicative of zero PPM target gas and using the slope of the initial and/or previous calibration line (e.g., slope of initial and/or previous calibration line connecting the initial and/or previous zero and span calibration points). The machine-executable instructions may also comprise instructions for any of the other methods described herein.

For another example, the sampling system can perform a method to, for example, select a source of gas having a zero concentration of the target gas, which may be ambient air at substantially similar humidity and temperature as the gas from the breathing circuit.

Delivery Sub System Overview

Gas delivery subsystem 105 can include, but is not limited to, a delivery gas pressure sensor(s) 109; delivery flow control valves 111, 113, and 115; a delivery gas flow sensor(s) 117; delivery gas flow restrictor(s) 119; memory(s) 143; and a processor(s) 145.

In exemplary embodiments, gas delivery subsystem 105 can deliver therapeutic gas, at a desired set dose (e.g., a desired concentration), to a patient. For example, gas delivery subsystem 105 can wild stream blend therapeutic gas (e.g., NO, etc.) into patient breathing gas in breathing circuit 126, affiliated with ventilator 104, as a percentage of the patient breathing gas. To at least wild stream blend therapeutic gas (e.g. NO, etc.) into patient breathing gas, gas delivery subsystem 105 can include and/or receive NO from a NO source 103, for example, via a delivery line 121 that can also be in fluid communication with an injector module 123, which in turn can also be in fluid communication with the inspiratory limb of breathing circuit 126 affiliated with ventilator 104.

As used herein, "wild stream blended proportional", "wild stream blending", and the like, relates to stream blending, where the main flow stream is an uncontrolled (unregulated) stream that is referred to as the wild stream, and the component being introduced into the wild stream is controlled as a percentage of the main stream, which may typically be blended upstream (or alternatively downstream) of the main stream flowmeter. In various embodiments, the inspiratory flow may be the "wild stream" as the flow is not specifically regulated or controlled, and the nitric oxide is the blend component that is delivered as a percentage of the inspiratory flow through a delivery line.

Ventilator 104 can deliver breathing gas to patient 102 via inspiratory limb 127 of patient breathing circuit 126, while patient expiration can flow via an expiratory limb 129 of patient breathing circuit 126, at times, to ventilator 104. With injector module 123 coupled to inspiratory limb 127 of breathing circuit 126, NO can be delivered from gas delivery subsystem 105 to injector module 123, via delivery line 121. This NO can then be delivered, via injector module 123, into inspiratory limb 127 of patient breathing circuit 126 affiliated ventilator 104 being used to deliver breathing gas to a patient 102.

To regulate flow of NO through delivery line 121 to injector module 123, and in turn to a patient 102 receiving breathing gas from inspiratory limb 127 of patient breathing circuit 126, therapeutic gas delivery system 100 can include one or more flow control valves 111, 113, and 115 (e.g., proportional valves, binary valves, etc.). For example, with flow control valves 111, 113, and/or 115 open, NO can be delivered to patient 102 by flowing through delivery line 121 to injector module 123, and in turn into inspiratory limb 127 of patient breathing circuit 126 and to patient 102.

In at least some instances, NO delivery system 100 can include one or more therapeutic gas flow sensors 117 that can measure the flow of therapeutic gas through flow control valves 111, 113, and 115 and/or delivery line 121, in turn enabling measurement of the flow of therapeutic gas to injector module 123, and in turn to patient 102. Further, in at least some instances, injector module 123 can include one or more breathing circuit gas (BCG) flow sensors 131 that can measure, and communicate to the delivery system, the mass and/or volume flow rate(s) of at least patient breathing gas in the inspiratory line of the breathing circuit passing through injector module 123, and in turn to patient 102. Although shown as being at injector module 123, BCG flow sensor 131 can be placed elsewhere in the inspiratory limb 121, such as upstream of the injector module 123. Also, instead of receiving flow information from BCG flow sensor 131, the delivery system may receive flow information directly from the ventilator 104 indicating the flow of breathing gas from ventilator 104.

In exemplary embodiments, therapeutic gas flow (e.g., NO gas flow) can be wild stream blended proportional (also known as ratio-metric) to the breathing gas (e.g., air) flow to provide a desired set dose concentration of the therapeutic gas (e.g., NO) in the combined breathing gas and therapeutic gas. For example, a user can input a desired set dose and the delivery system can deliver this set dose to patient 102. Further, NO delivery system 100 can execute, for example, using machine-executable instructions, a delivered concentration calculation that confirms that the desired concentration of the therapeutic gas (e.g., NO) is in the combined breathing gas and therapeutic gas using the known concentration of therapeutic gas source 103; the amount of breathing gas flow in the patient circuit using information from BCG flow sensor 131 and/or from ventilator 104; and the amount of therapeutic gas flow in delivery line 121 to injector module 123 (and in turn to patient 102) using information from therapeutic gas flow sensor 117.

In exemplary embodiments, therapeutic gas delivery system 100 can allow a user to input a desired set dose of the therapeutic gas (e.g., NO in PPM) and the therapeutic gas delivery system can confirm that the desired set dose of the therapeutic gas is being delivered to the patient by calculating the delivery concentration (e.g., as described above) as well as using gas sampling system 106 to confirm the desired set dose of the therapeutic gas (e.g., NO) is being delivered to the patient. In some instances a problem may arise where the sensor does not accurately report the dose of therapeutic gas being delivered to the patient.

Gas Sampling Sub System Overview

Gas sampling system 106 can include, but is not limited to numerous sensors such as, but not limited to, an electrochemical NO gas sensor 108, which may have a catalytic type electrode material with high catalytic activity for the electrochemical reactions of the sensor, a catalytic type electrochemical nitrogen dioxide gas sensor 110, and a galvanic type electrochemical oxygen gas sensor 112, to name a few; a sample gas flow sensor(s) 114; a sample pump(s) 116; sample system valve(s) 118; a processor(s) 120; and memory(s) 122. Sensors 108, 110, and 112 can be in series and/or parallel and/or can be in any order. For ease, sensors 108, 110, and 112 are illustratively depicted as being in series. This is merely for ease and is in no way meant to be a limitation. In various embodiments, the NO sensor may be an electro-chemical sensor, which may comprise two electrodes, including a sensing and a counter electrode, separated by a thin layer of electrolyte.

In exemplary embodiments, gas sampling subsystem 106 can sample and/or measure the concentration of various gases being delivered to a patient. The concentration of NO being delivered to patient 102 can be sampled and exposed to NO sensor 108, which in turn can output information indicative of the concentration of NO in the breathing gas (e.g., NO PPM). For example, a sample of the gas being delivered to the patient can be sampled via a sample line 124 that is in fluid communication with inspiratory line 127 of breathing circuit 126 affiliated with breathing apparatus 104. This gas sample from inspiratory line 127, via sample line 124, can flow and/or be pulled to the gas sensors (e.g., NO sensor 108). Flow in sample line 124 can be regulated via valve 118 and/or sample pump 116. Sample line mass or volume flow can be measured using flow sensor 114. Sample line 124 can also be in fluid communication with a gas sample conditioner 128 that may condition the sample gas, for example, by extracting fluids, placing the sample at the appropriate humidity, removing contaminants from the sample, and/or can condition the sample gas in any other way as desired.

In exemplary embodiments, gas sampling system 106 can perform calibrations (e.g., baseline calibrations, span calibrations, etc.) of the gas sensor (e.g., catalytic type electrochemical gas sensor) by sampling and/or measuring the concentration of target gases in a controlled sample (e.g., baseline sample, span sample, etc.), where a span sample is a target gas (i.e., nitric oxide) with a specific known and controlled concentration within a range of interest (e.g., 10 PPM, 25 PPM, 50 PPM, 80 PPM, etc.) and/or where a baseline sample is a gas containing zero concentration of a target gas (i.e., conditioned ambient air containing zero nitric oxide). For example, a sample of ambient gas 130 and/or span gas 132 can be sampled via a sample line 134. This gas sample from ambient gas 130 and/or span gas 132, via sample line 134, can flow and/or be pulled to the gas sensors (e.g., NO sensor 108). Flow in sample line 134 can be regulated via valve 118 (e.g., a three way valve, etc.) and/or sample pump 116. Sample line flow can be measured using flow sensor 114.

In exemplary embodiments, sample line 134 can also be in fluid communication with a gas sample conditioner 136 that may condition the sample gas, for example, by extracting fluids, placing the sample at the appropriate humidity, removing contaminants from the sample, and/or can condition the sample gas in any other way as desired. For example, the ambient air (e.g., ambient gas 130) used for the baseline calibration may be scrubbed of any undesirable gases using a scrubber material. By way of example, this scrubbing material can be an inline Potassium permanganate scrubber material capable of scrubbing the ambient air removing NO and $NO_2$. With the NO and $NO_2$ removed from the ambient air, the scrubbed air can be used for a zero calibration as these undesirable gases have been removed hence they are at 0 PPM. If needed, a similar technique (e.g., using an inline scrubber material) can be done for span gas.

Sensor Overview

In exemplary embodiments, the electrochemical gas sensor used in therapeutic gas delivery system 100 can be a three terminal catalytic type electrochemical gas sensor and/or a four terminal catalytic type electrochemical gas sensor. An exemplary three terminal catalytic type electrochemical gas sensor 200 is illustratively depicted in FIG. 2A and an exemplary four terminal catalytic type electrochemical gas sensor 200' is illustratively depicted in FIG. 2B.

Generally speaking, both three and four terminal catalytic type electrochemical gas sensors include a sensing electrode 202 (anode or working electrode) and a counter electrode 206 (cathode) separated by a layer of electrolyte 208. Further, these sensors can also include a capillary diffusion barrier 210 that can be used to control the gas reaction rate in the sensor (e.g., reacting with the sensing electrode) and/or a hydrophobic barrier 212 that can be used to prevent aqueous liquid electrolyte from leaking from the sensor or drying out from lost water vapor. In use, gas flowing into the sensor passes through a capillary diffusion barrier 210, diffuses through a hydrophobic barrier 212, and subsequently reaches and reacts with sensing electrode 202. The gas sensor can be exposed to samples of the therapeutic gas, the ambient gas, and/or the span gas.

Gas that reaches sensing electrode 202 reacts at the surface of sensing electrode 202 by an oxidation or reduction mechanism catalyzed by the electrode materials specifically selected for the gas of interest. In other words, when oxidation occurs at sensing electrode 202 (anode) reduction occurs at counter electrode 206 (cathode) and a current can be created as the positive ions flow to the cathode and the negative ions flow to the anode. Gases such as oxygen, nitrogen dioxide, and chlorine which are electrochemically reducible can be sensed at the cathode while those which are electrochemically oxidizable such as carbon monoxide, NO, and hydrogen sulfide can be sensed at the anode. Connecting a resistor and/or current to voltage amplifier 214 across the electrodes (sensing electrode 202 and counter electrode 206), an electrical current proportional to the gas concentration flows between the anode and the cathode (sensing electrode 202 and counter electrode 206). This current can be measured to determine the gas concentration. Because a current is generated in the process, these sensors can be described as an amperometric gas sensor, a micro fuel cell, and/or the like, to name a few.

Figure 2A:
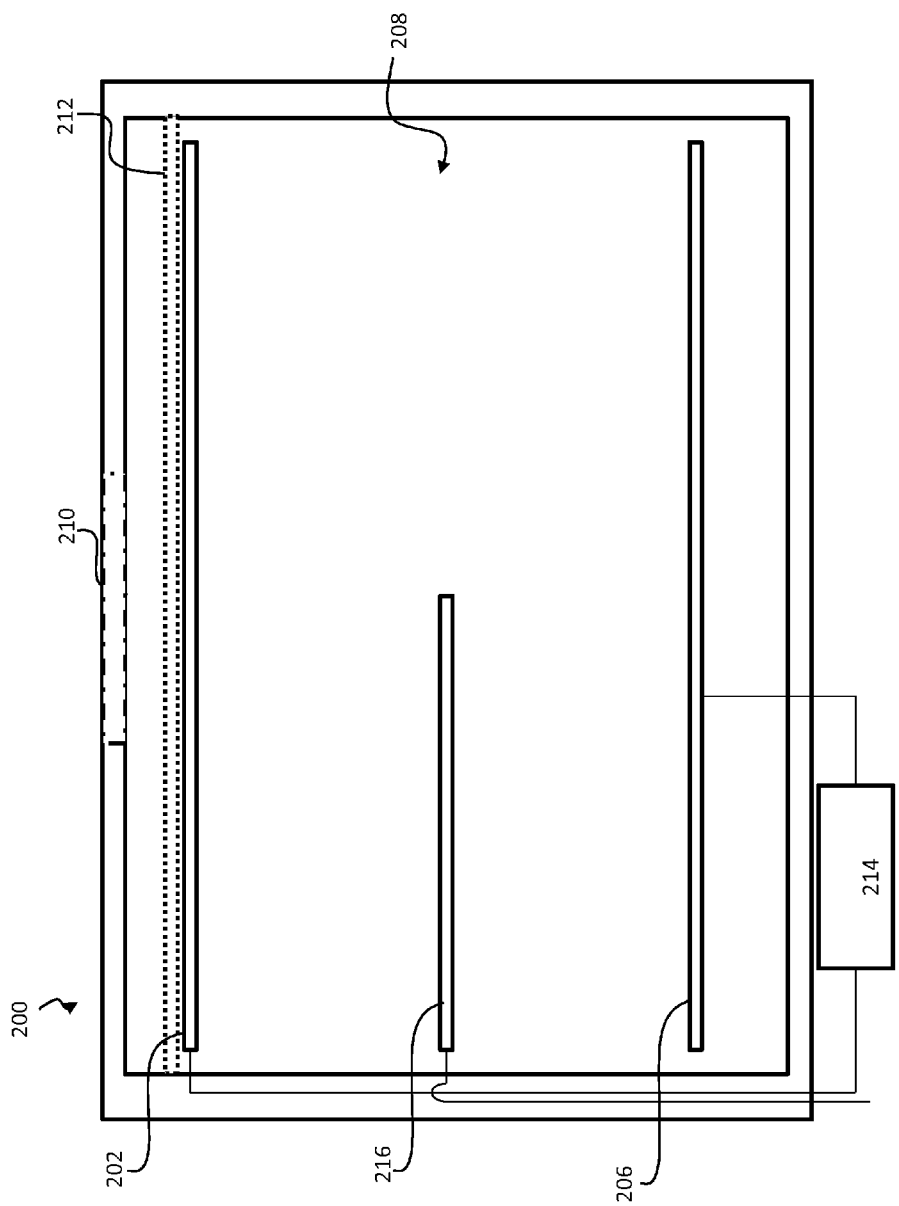
FIG. 2A illustratively depicts an exemplary three terminal catalytic type electrochemical gas sensor, in accordance with exemplary embodiments of the present invention.

In some instances, electrochemical sensor 200 can also include a third electrode (e.g., a three terminal electrochemical sensors), as illustrated in FIG. 2A, that can act as a reference electrode 216. In electrochemical sensors that include a reference electrode, sensing electrode 202 can be held at a fixed potential relative to the reference electrode (from which no current is drawn) so both the reference electrode and the sensing electrode maintain a substantially constant voltage potential (e.g., maintained by a counter current source). This constant electrical potential ensures target gas selectivity or prevention of cross-sensitivity to other non-target gases.

Figure 2B:
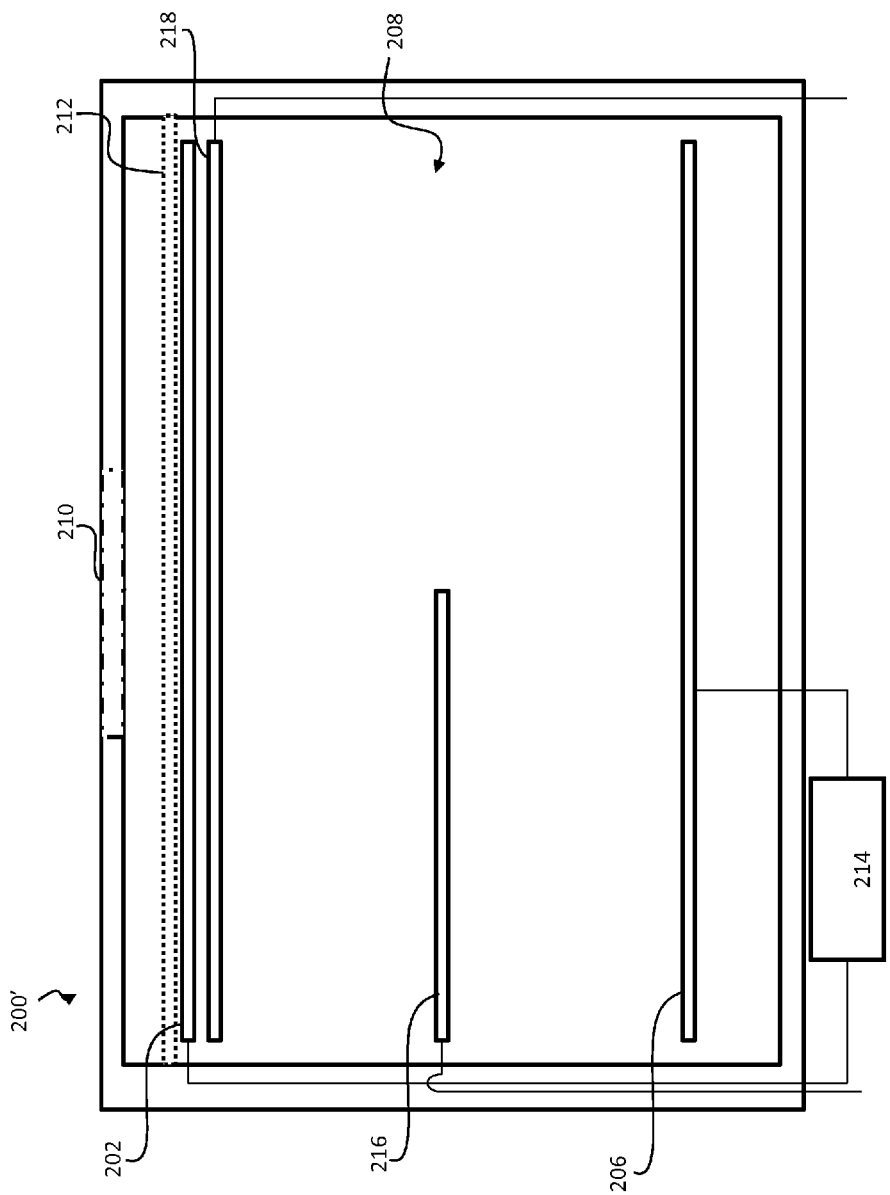
FIG. 2B illustratively depicts an exemplary four terminal catalytic type electrochemical gas sensor, in accordance with exemplary embodiments of the present invention.

In further instances, electrochemical sensor 200 can include a fourth electrode (e.g., a four terminal electrochemical sensor), as illustrated in FIG. 2B, that can act as an auxiliary electrode 218. This auxiliary electrode 218 can be used to subtract output sensitivity changes not related to the concentration of the target gas that may be due to local effects on electrochemical sensor 200.

An electrochemical sensor 200 may be wired or installed in a suitable socket, where the wiring or socket may provide for or allow detection of the number of electrodes (e.g., by the presence or absence of a voltage or current to or from the electrode.

Sensor Drift

In exemplary embodiments, catalytic type electrochemical gas sensors (e.g. NO sensors, three terminal electrochemical sensors, four terminal electrochemical sensors, etc.) operate by reacting with the gas of interest (e.g., target gas, NO, etc.) thereby producing an electrical current that is, generally speaking, proportional to the concentration of the gas of interest. For example, the greater the concentration of NO that reacts with the NO sensor the greater the electrical current produced by the sensor. Hence, using this proportional relationship, the electrical current produced by the sensor can be used to determine the concentration of the NO gas being sampled and/or delivered to the patient.

Following the example of delivering therapeutic NO gas, using the output from the NO sensor the concentration of NO can be determined and provided to a user, for example, on the user display. This can allow the user to confirm that the set dose (e.g., desired concentration of NO) is actually being delivered to the patient. As noted above, the concentration of therapeutic gas (NO) in the inspiratory flow being delivered to the patient can be calculated, for example, using delivered concentration calculation; however, at times, this calculated concentration of therapeutic gas may not be displayed to the user. Accordingly, output from the NO sensor may be the only, or preferred, way for the user to confirm the correct therapeutic dose is actually being delivered to the patient, drift in the NO sensor can be particularly problematic.

Another challenge specific to therapeutic gas delivery, that is not present for conventional use of catalytic NO sensors (e.g. smokestack emission monitoring), is that sample flow rates from the breathing circuit must be kept to a minimum as to not interfere with the ventilation therapy (e.g. less than 250 ml/min, which may sometimes be less than the minimum value specified by the electrochemical cell manufacturer). Gas sample flow rates can appear as leaks in the circuit from the perspective of ventilation therapy (e.g. the ventilator). When the therapeutic NO gas monitor is sampling from the breathing circuit, the reported ventilator inspiratory flows (and volumes) are greater than the measured expiratory flows (and volumes). This is referred to as inspiratory/expiratory volume mismatch—the patient may not receive the specified tidal volume. For ventilators with spontaneous ventilation modes (e.g. actively detect and support patient's inhalation effort) gas sample flow rates may interfere with breath detection algorithms and/or breath detection sensitivity. These ventilators monitor expiratory flows less than inspiratory flows to detect breaths. When a gas sample flow rate is being drawn from the inspiratory limb of a breathing circuit the result is that the expiratory flow will measure to be less than the inspiratory flow. All of the effects described above can both have an impact on the patient's ventilation therapy as well as lead to confusion for the caregiver.

Figure 3:
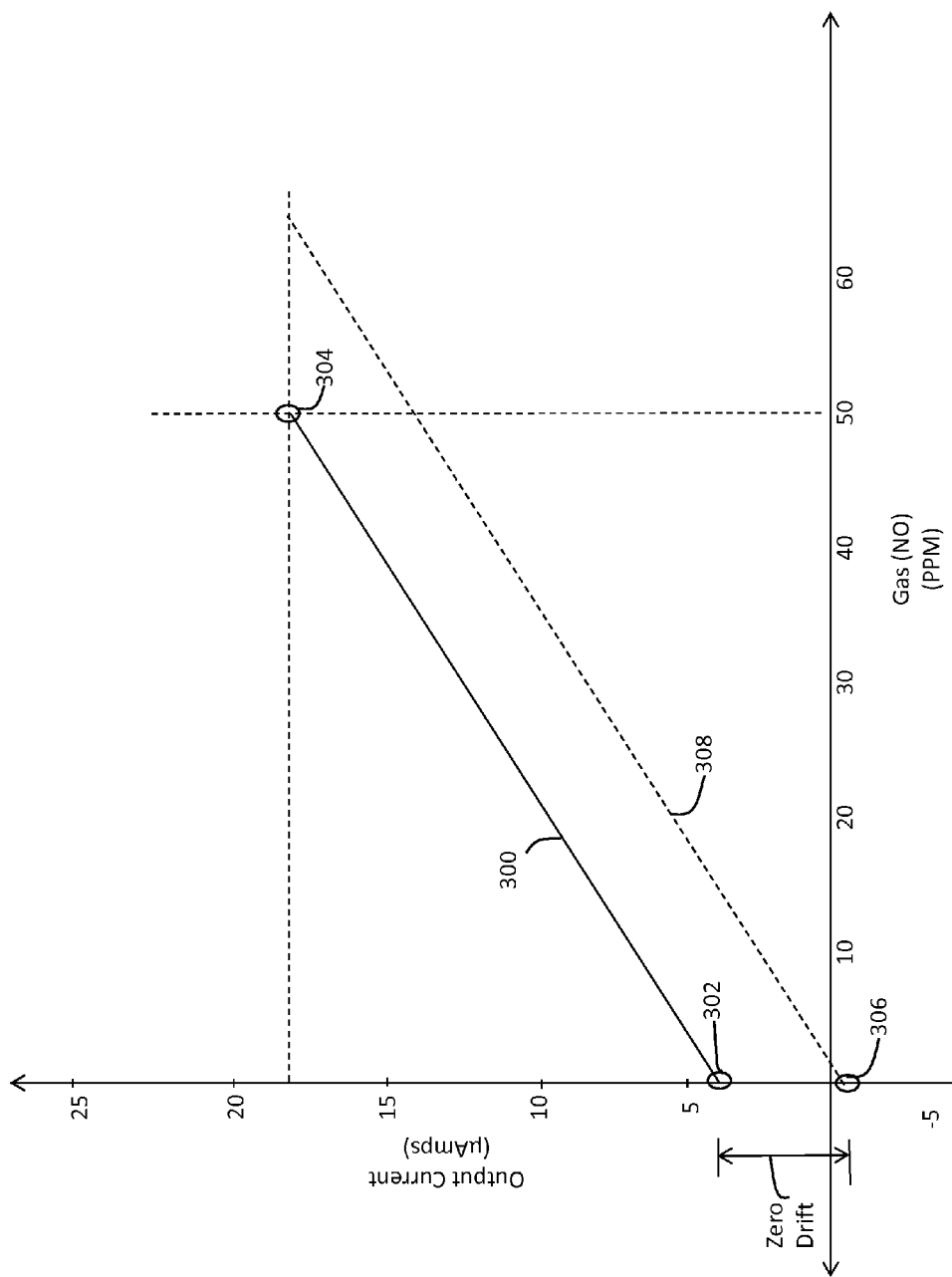
FIG. 3 illustratively depicts an exemplary two-point linear interpolation calibration line, in accordance with exemplary embodiments of the present invention.

Referring to FIGS. 1A-1B and 3, because of this proportional (near linear) relationship, a two-point linear interpolation calibration line 300 can be established where a range of electrical output from the sensor corresponds to a range of gas concentrations, including 0 PPM concentrations. This calibration line can be established by exposing NO sensor 108 to two known gas sources, such as, one containing zero target gas such as ambient source 130 and span source 132 containing a known concentration of target gas. For ease, ambient source 130 and span source 132 are depicted as being in fluid communication with sample line 134. This is merely for ease and is in no way meant to be a limitation. For example, ambient source 130 and/or span source 132 can be in fluid communication with sample line 124. Using ambient source 130, an initial baseline signal (also known as "base current") calibration point 302 can be determined by exposing NO sensor 108 to ambient source 130 (e.g., conditioned ambient that can have 0 PPM of NO and/or that can be inclusive of environmental temperature and humidity) to establish an output current for a zero concentration of a target gas of interest (e.g., approximately 4.5 micro-amps output current for 0 PPM of NO). Using span source 132, a span calibration point 304 can be determined by exposing NO sensor 108 to span source 132 (e.g., calibration gas) to establish an output current for another known concentration (span concentration) of a target gas of interest (e.g., approximately 17 micro-amps output current for 50 PPM of NO). Connecting span point 304 and zero point 302, a linear calibration line 300 for the sensor can be established so a user can determine the concentration of gas based on the output current of NO sensor 108. Of course additional points can be determined using a similar technique and/or other known techniques can be used to produce a reference calibration line. The output values of the sensor(s) for the different calibration points may be stored in memory.

The linear calibration line 300 may be stored in memory as an intercept value for the zero point 302 and a slope calculated from the zero point and span point 304, or as a set of values from multiple span points 304 of different concentrations and a zero point 302.

However, during long periods of continuous use, drift (offset) in the output current established during the initial calibration line (e.g., initial baseline calibration, base current, initial span calibration, etc.) can occur. In at least some instances, drift can occur because, amongst other things, the catalytic type electrochemical cell becomes saturated. Drift can cause the output displayed to the user, for example, in display 107(b) to be incorrect. In turn, the user may not be able to confirm that the desired set dose is actually being delivered to the patient. This can lead to numerous problems and confusion. For example, with an incorrect quantity shown in display 107(b) the user may believe the incorrect concentration shown in display 107(b) is the actual concentration being delivered to the patient. Based on this incorrect information the user may adjust set dose (e.g., NO PPM) and thereby the concentration (e.g., of NO) being delivered to the patient. In turn, this new adjusted concentration could be an incorrect dosage for the patient even though the displayed dosage may indicate that the quantity being delivered to the patient is the desired set quantity.

Desaturation

To correct for this drift, the sensor can be exposed for an extended period of time (e.g., hours, 24 hours, etc.) to ambient air and/or a source containing zero concentration of the target gas thereby allowing the sensor to de-saturate. As the sensor slowly de-saturates the original sensor sensitivity slowly returns. After de-saturating, the original calibration line most often can be used and, in some instances, a new baseline calibration and span calibration can be performed to generate a new calibration line. Although de-saturating the sensor may be used to correct drift the extended period of time needed to de-saturate the sensor may not be acceptable for an NO sensor used in a therapeutic gas delivery system because, for example, the sensor will be offline during the de-saturation period.

Zero and Span Calibration

In exemplary embodiments, unlike de-saturating the sensor, to compensate for drift a baseline calibration and/or a span calibration can be performed when the sensor is still at least partially saturated. Using this output from the baseline calibration and/or span calibration, a new calibration line that compensates for drift can be generated while the sensor is still at least partially saturated. To perform a span calibration the sensor needs to be exposed to a span source (e.g., a tank containing a known concentration of the target gas, a 50 PPM canister of NO gas, etc.) and to perform a baseline calibration the sensor needs to be exposed to a source containing zero target gas (e.g., ambient air containing no target gas).

Conducting a span calibration can be more labor intensive than a baseline calibration as it requires a container having a known concentration of the target gas whereas a baseline calibration can use ambient air (e.g., conditioned ambient air). In light of at least the above, it can be more desirable to perform a baseline calibration to, amongst other things, reduce complexity of the system, reduce the footprint associated with the device (e.g., in areas where critical care may be needed, in areas where the footprint may be costly or of concern, etc.), and/or ease use of the system. Accordingly, in exemplary embodiments, to compensate for baseline drift, automatically and/or manually, a baseline calibration can be performed to generate a new calibration line that compensates for drift in the electrochemical sensor, for example, when the sensor is at least partially saturated.

In exemplary embodiments, a new calibration line that compensates for drift of the at least partially saturated sensor can be generated using the sensor output for a new baseline calibration and the slope of the initial and/or previous calibration line. The sensor drift can be the difference in the output from the new baseline calibration 306 and the initial and/or previous baseline calibration 302. By way of example, the quantity of this drift (offset) from the initial baseline current 302 (4.5 microamps for 0 PPM of NO) to a new baseline current 306 (−1.0 microamp for 0 PPM of NO) can be determined when exposing the sensor to 0 PPM of NO (e.g., conditioned ambient air). Applying the initial and/or previous calibration line's slope to the new baseline current a new calibration line 308 can be generated. This new calibration line that compensates for drift can then be used to determine the concentration of target gas (NO) being delivered to the patient.

In exemplary embodiments, reducing the duration of time it takes to perform a calibration (e.g., performed in the calibration schedule described below in greater detail) can be important because it can minimize the time that the monitoring system is offline as, in at least some instances, at least some gas concentration alarms (low/high NO alarms, low/high $O_2$ alarms, high $NO_2$ alarms, etc.) can be inactive during this time. At least some alarms may be inactive during baseline calibration to prevent false and/or nuisance alarms. Accordingly, in exemplary embodiments, the time to perform a baseline calibration and/or time offline can include both the response time of the catalytic type electrochemical sensor required to obtain the zero offset reading (e.g., the output indicative of 0 PPM when the sensor may be at least partially saturated) and the response time of the catalytic type electrochemical sensor back to the set dose (e.g., time required for sensor to provide the concentration of the target gas when re-exposed to the target gas at the set dose). At the time the calibrations are being performed and/or the alarms are off-line, an indicator may be provided to a user to inform them that calibration is being performed and/or the alarms are currently off-line, so users do not come to a mistaken conclusion that the system is not functioning properly.

In exemplary embodiments, the quantity of this drift (offset) in the baseline (zero) current output can be determined by exposing the sensor (e.g., NO sensor) to a known 0 PPM concentration of the gas of interest (e.g., NO), for example, using room air for a period of time (e.g., 3 minutes, etc.), where the period of time may be in the range of about 3 to 5 minutes to re-establish zero (e.g., within the therapeutic gas delivery system calibration line) and, after this period of exposure (e.g., to ambient air), the sensor may then require another period of time (e.g., 2 minutes, etc.), where the period of time may be in the range of about 1 to 2 minutes to stabilize to target gas. This drift can then be used to adjust the calibration line offset. By way of example, to determine the quantity of this drift (offset) in the initial baseline current output (4.5 micro amps for 0 PPM of NO), a new baseline current 306 (−1.0 micro amp for 0 PPM of NO) can be determined when exposing the sensor to 0 PPM of NO (ambient air). The now known baseline current shift (e.g., from 0 micro amps to −1 micro amps for 0 PPM of NO) can be applied with the slope of the initial and/or previous calibration line to report the actual NO gas concentration. In various embodiments, the calibration may take a period of time in the range of about 4 to 7 minutes and/or the system may be offline less than 10 minutes.

In exemplary embodiments, the period of time that the sensor is exposed to a known 0 PPM concentration (e.g., room air) can be determined and/or based on variables such as, but not limited to, the reaction rate of the sensor to the target gas (e.g., reaction rate of the sensor with air, reaction rate of the sensor with NO, etc.); the physical device size; cell gas exchange rates; thermal impedance to surrounding environment; humidity; sample gas flow rate (e.g., which can be secondary), for example, which may affect output signal rise and fall times; and/or any combination or further separation there of; to name a few. In various embodiments, a gas sensor may be exposed to a gas for about 5 seconds to about 15 seconds, or about 5 seconds to about 10 seconds to obtain a reading.

In exemplary embodiments, the output of a sensor, which may be in microamps, may be converted to a digital value (referred to as counts) by an analog-to-digital converter circuit. The rate of change of the NO sensor output can be monitored and compared against predetermined thresholds deemed "stable". To determine if the sensor output is stable, the sensor output may be monitored and/or recorded over a period of time, and the average, minimum, and maximum vales observed during the monitoring period compared to determine how much the sensor output has varied and/or how uniform the sensor output was over the monitored and/or recorded over a period of time, for example, ADC (Analog to Digital) count per unit time, may be 1.5 to 2.5 ADC counts per 10 seconds. The ADC counts may have a sampling rate (e.g., 10 measurements per second), and may be sampled over a set period of time (e.g., 10 seconds). For example, a current in microamps may be converted to a related number of counts in one sampling period of 0.1 second, and the counts generated over 10 seconds summed and averaged. The number of counts measured over a period may be stored in memory. If the sensor output (e.g., in microamps or ADC counts) is outside the stable threshold during the monitoring period, monitoring may be continued until the sensor output is within the stable threshold, for example, 1 ADC count variation or less over a 10 second monitoring period. It has been found that, in at least some instances, sensor response to changes in concentration of the target gas (e.g., changes in set dose of NO) may respond more quickly in newer sensors and/or with smaller absolute changes in concentration (e.g., smaller absolute changes in set dose). Accordingly, in exemplary embodiments, systems and methods of the present invention can adapt to differing rates of change of sensor output to minimize duration of time offline. For example, the calibration schedule and/or set dose change response algorithm, described below in greater detail, can factor in the differing rates of change of sensor output to, for example, minimize the duration of time offline (e.g., duration of time the NO sensor is offline, etc.). The sensor signal may exhibit an asymptotic approach to a final value over time. By monitoring the sensor output for variations over the monitored and/or recorded over a period of time, the calibration may be concluded when the sensor output is within the stable threshold, which may provide a value within 99% of the full signal.

In exemplary embodiments, the duration of time the catalytic type electrochemical sensor is exposed to ambient air when performing baseline calibrations, in at least some instances, can be required to be the same for all baseline calibrations in a calibration schedule. For example, all baseline calibrations in the same calibration schedule can be required to be performed over the same length of time, such that the sensor is exposed to the gas for the same length of time each time a calibration is conducted. For example, the reading from a gas sensor may be taken at the end of a 5 second exposure time for each baseline calibration. By taking a reading for the same exposure time each time a calibration is conducted, the sensor has the same period of time to respond and produce the same final value. From research Applicant found that when exposing the sensor to room air (e.g., initiating an auto calibration), output from the sensor initially decreases substantially rapidly for a short period of time, where the sensor output approaches 90% of final value in approximately the first 30 seconds of exposure. The time period may vary based on the responsiveness of the sensor, where the sensor output may approach 90% of the final value in approximately the first minute or two of exposure, and then the sensor output slowly decreases (e.g., exponential decay) to baseline over a longer period of time (e.g., hours of exposure, days of exposure, weeks of exposure, etc.). This later slower decay over a longer period of time can be the time required for desaturation. However, for drift compensation of the senor using baseline calibrations, applicant found that this slower decrease in sensor output over a longer period of time may be less significant (e.g., than the initial substantially rapid decrease in sensor output) for determining baseline drift compensation. Noting this initial rapid decrease in sensor output, in exemplary embodiment, the duration of time for exposing the sensor to ambient air (e.g., baseline zero calibrations) can be required to be the same for all, or at least some, of the baseline zero calibration.

Calibration Schedule (Set Dose Change)

Although the baseline calibration may be used to compensate for drift, when using catalytic type electrochemical sensors (e.g., NO sensors) in a therapeutic gas delivery system that delivers the therapeutic gas (e.g., NO) to a patient (e.g., for a prolonged period of time) such baseline calibrations can require the signal from the electrochemical sensor to go offline. As noted above, having the electrochemical sensor go offline can be problematic. because, for example, when the sensor goes offline users (e.g., doctors, nurses, etc.) may not be able to monitor NO delivery and/or modify delivery of NO to a patient. In addition, a reading different that the expected set dose or no reading at all may be displayed to a user during this "blackout" period, which may cause concern or lead to confusion. Conversely, if the sensor is not re-zeroed (e.g., baseline calibrated, etc.) then the measured concentration of NO may not be accurate. The above can be problematic because, although it may be preferable from at least an accuracy standpoint to perform baseline calibrations very frequently, frequent baseline calibrations may not be acceptable from at least a therapeutic standpoint as the therapeutic gas delivery system's ability to use the electrochemical sensor goes offline during the baseline calibration. In at least some embodiments, the electrochemical sensor may be offline for a period of time in the range of 5 min to about 10 min, or for a maximum time period of 10 minutes during the baseline calibration.

Noting the above, Applicant conducted extensive research and found that electrochemical gas cell sensitivity drift can be related to the absolute change in concentration of the therapeutic gas (e.g., absolute change in NO set dose) where the larger the absolute change the more drift occurred. Noting this relationship, the frequency of calibrations (e.g., baseline calibrations, etc.) performed on catalytic type electrochemical sensors (e.g., NO sensor) can be reduced by factoring in the absolute concentration change of NO being delivered to the patient (e.g., the absolute concentration change of the set dose of NO). Hence a schedule (e.g., calibration schedule), that factors in the absolute concentration change of NO being delivered to the patient (e.g., the absolute concentration change of the set dose of NO), can be used to ensure greater accuracy of the sensor while reducing the duration of time and/or quantity of times that the sensor goes offline. Accordingly, in exemplary embodiments, the frequency of baseline calibrations in a calibration schedule can be based on the absolute change in concentration of NO being delivered to the patient (e.g., absolute change in set dose) wherein the frequency of baseline calibrations may be more frequent (e.g., shorter intervals between baseline calibrations) for a greater absolute changes in concentration of NO being delivered to the patient (e.g., absolute change in set dose) and/or the frequency baseline calibrations may be less frequent (e.g., longer intervals between baseline calibration) for lesser absolute changes in concentration of NO being delivered to the patient (e.g., absolute change in set dose). The interval between calibrations may increase proportionally with an absolute change in the set dose. The duration of room air zeroing or span calibration can be insignificant for changes in cell saturation or desaturation.

Figure 5:
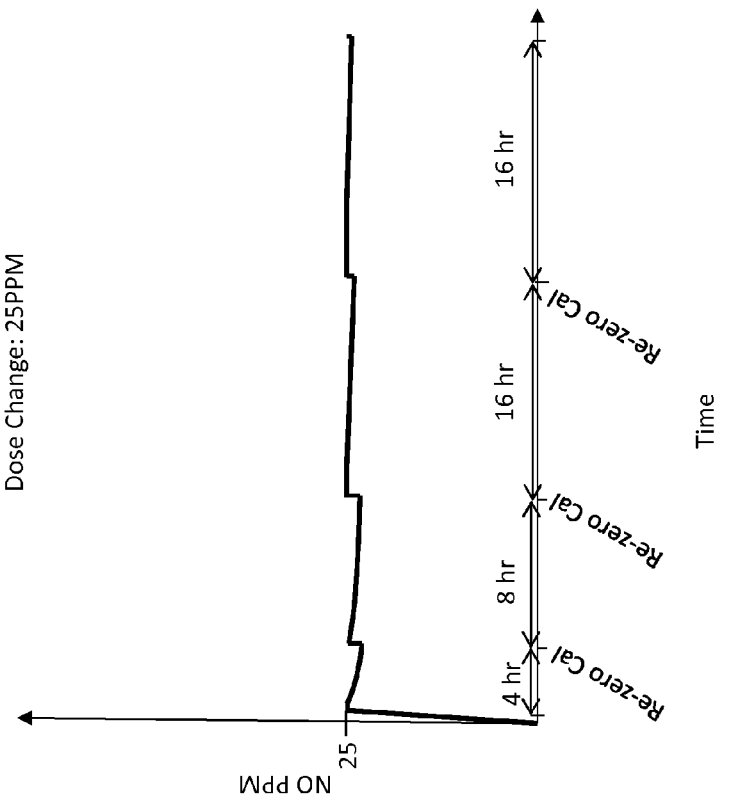
FIGS. 4-9 illustratively depict exemplary drifts of exemplary catalytic type electrochemical gas sensors in exemplary systems for delivering therapeutic nitric oxide gas to a patient, in accordance with exemplary embodiments of the present invention.
Figure 4:
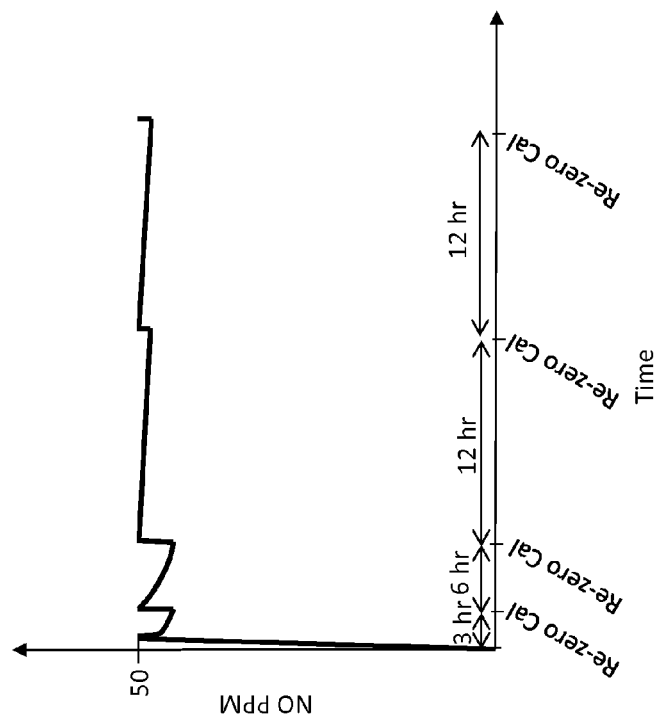

Referring to FIGS. 4-5, demonstrative graphs illustrate drift in the desired set dose (e.g., as displayed to the user to confirm an accurate dose of NO is being delivered to a patient) and baseline calibrations, used in an exemplary calibration schedule, of an exemplary four terminal catalytic type electrochemical NO gas sensor with respect to time for a patient who may actually be receiving the desired set dose. That is, the patient may be receiving the correct set dose; however, the displayed amount to the user shows the incorrect amount being delivered. For example, the demonstrative graph illustrated in FIG. 4 shows drift and baseline calibrations for a patient receiving a set dose of 50 PPM of NO and the demonstrative graph illustrated in FIG. 5 shows drift and baseline calibrations for a patient receiving a set dose of 25 PPM of NO. It will be understood that the dosage to the patient can remain at the desired set dose (e.g., set dose of 50 PPM NO, set dose of 25 PPM NO, etc.) even though the readout from the sensor may drift (e.g., which in turn may be displayed to the user of a therapeutic gas delivery system as a different PPM being delivered to the patient). In various embodiments, the type of electrochemical gas sensor may be entered into memory, for example by a user or by automatic detection of the electrochemical gas sensor by the system controller. In various embodiments, the type of electrochemical gas sensor may be detected by monitoring a potentiostat and detecting a change in voltage and/or current for an electrode, and/or detecting the presence of a current or voltage at a prong in a socket configured for the sensor.

In exemplary embodiments, a recalibration schedule can be used to determine when the baseline calibrations occur and/or implemented in response to a set dose change, at times automatically. By way of example, the patient can begin receiving the set dose of NO at 50 PPM (e.g., as set by the user) thereby exposing the NO sensor to 50 PPM of NO; however, as shown the sensor begins drifting (e.g., giving an indication that the patient may be receiving a lower PPM dosage than what was set and/or actually being delivered to the patient). To correct this drift a baseline calibration can be performed on the sensor after a desired amount of time (e.g., three hours, four hours, six hours) of exposure to NO. This interval may be measured using an internal clock or a real time clock within the system or system controller, wherein the internal clock or a real time clock may be used to identify a time for executing a calibration. After performing a baseline calibration, the sensor can then be exposed to NO again. Subsequently the sensor may again begin drifting. To correct this drift a baseline calibration can again be performed on the sensor after another desired amount of time (e.g., six hours, eight hours, twelve hours) of exposure to NO. This interval may be measured from the previous interval relatively using the internal clock or absolutely using the real time clock to identify a time for the subsequent calibration. After performing the previous baseline calibration, the sensor can then resume being exposed to NO at 50 PPM and again the sensor may begin drifting. To correct this drift a baseline calibration can be performed on the sensor after yet another desired amount of time (e.g., twelve hours) of exposure to NO. In various embodiments, the maximum interval between calibrations may be 24 hours, so that a minimum of one calibration is run per day.

In exemplary embodiments, the recalibration schedule(s) may be stored in the controller memory. There may be one or more recalibration schedule(s), where a recalibration schedule comprises one or more values indicating one or more time intervals between calibration operations. By way of example, a method of calculating a recalibration schedule may be based on 150 PPM-hours and include dividing 150 PPM by the set dose to determine the number of hours of the time interval between calibration operations. For example, if after a set dose of 50 PPM for 3 hours, 150 PPM-hours would have accumulated. If then, a new dose of 25 PPM was now set, an accumulation of 6 hours (150 PPM-hours) would occur before another baseline calibration. Subsequent intervals between calibrations may be double the earlier interval up to 12 hours, and/or up to 24 hours thereafter.

In an exemplary embodiment, the PPM-hours (e.g., X PPM-hours) may be doubled (e.g., 2×PPM-hours) to calculate the interval until the second calibration, and doubled again to calculate the interval until the third calibration, etc., until the maximum 24 hour calibration is reached. By way of example, the 150 PPM-hours may be doubled to 300 PPM-hours to calculate the interval until the second calibration, and doubled again to calculate the interval until the third calibration, etc., until the maximum 24 hour calibration is reached. For example, a change in set dose from 10 PPM to 60 PPM would produce and absolute change of 50 PPM, so the interval between the set dose change and the first calibration would be 150 PPM-hours/50 PPM=3 hours. The next interval would be 300 PPM-hours/50 PPM=6 hours after the first calibration, as measured by the clock, followed by an interval of 600 PPM-hours/50 PPM=12 hours later. The following interval would be 1200 PPM-hours/50 PPM=24 hours later, which can also the maximum interval, so no further calculations are done, and each subsequent interval between calibrations remains 24 hours. It has been found that the greatest amount of drift occurs during the first 24 hours after a set dose change, and drifts only slightly over a 24 hour period if the concentration remains the same for that period.

As noted above, in exemplary embodiments, calibration schedules can factor in the absolute change in the set dose of NO being delivered to the patient, wherein, larger absolute changes in set dose can require more frequent baseline calibrations than smaller absolute changes, where for example a positive or negative change of 10 PPM has less of an impact on the interval between calibrations than a positive or negative 50 PPM change. By way of example, FIG. 4 illustrates, amongst other things, an absolute change from 0 PPM NO being delivered to NO being delivered to a patient at 50 PPM (and thereby exposing an exemplary four terminal catalytic type electrochemical NO gas sensor to 50 PPM of NO), while FIG. 5 illustrates, amongst other things, at least one embodiment for an absolute change from 0 PPM NO being delivered to NO being delivered to a patient at 25 PPM (and thereby exposing the exemplary four terminal exemplary catalytic type electrochemical NO gas sensor to 25 PPM of NO). As can be seen by comparing FIG. 4 and FIG. 5, for a greater absolute change in concentration NO (e.g., as shown in FIG. 4) the drift is larger and therefor baseline calibrations may be more frequent than for a lesser absolute change in concentration of NO (e.g., as shown in FIG. 5). In various embodiments, the value for the number of PPM-hours may depend on the type of sensor installed and/or detected by the system controller, or may be set by a user for example. In some embodiments, the system may have a default schedule of auto-calibration every 24 hours.

Based upon the calculations using 150 PPM-hours, the 50 PPM change generates a first calibration interval of 150 PPM/50 PPM=3 hours, as shown in FIG. 4. Of course other PPM-hours are envisioned. For example, based upon the calculations using 100 PPM-hours, a 25 PPM change generates a first calibration interval of 100 PPM/25=4 hours, as shown in FIG. 5.

In exemplary embodiments, the frequency of baseline calibrations in a calibration schedule, which may be based on the absolute change in concentration of NO being delivered to the patient (e.g., set dose), can also depend on whether the catalytic type electrochemical sensor has three terminals or four terminals. In at least some instances, four terminal catalytic type electrochemical sensors may have calibration schedules that initially vary the duration between baseline calibrations and then have fixed durations between baseline calibrations. In at least some instances, three terminal catalytic type electrochemical sensor may have calibration schedules having fixed durations between baseline calibrations.

While not intending to be bound by theory, or to limit the scope of the invention in any way, it is presently believed that, although the auxiliary electrode in the four terminal catalytic type electrochemical sensor (e.g., NO sensor) may be intended to be used to cancel out localized effects seen on the sensing electrode that may produce and/or effect output (e.g., electrical current, ADC counts, etc.) from the sensing electrode not indicative of the target gas concentration, when used atypically the localized effects on the auxiliary electrode and the localized effects on the sensing electrode may not be the same initially; however, after prolonged exposure (e.g., 24 hours) to the same concentration NO (e.g., set dose remains constant) this difference between the auxiliary electrode and sensing electrode may become negligible. In other words, when the set dose changes, for four terminal catalytic type electrochemical sensors (e.g., NO sensors), there may be an initial period of non-steady state which is then followed by a steady state period. On the other hand, as a three terminal catalytic type electrochemical sensor (e.g., NO sensor) does not include this auxiliary electrode this effect does not occur. It is believed that this may be the reason why, for the same absolute change in NO, different calibrations schedules may be needed for three terminal catalytic type electrochemical sensors and four terminal catalytic type electrochemical sensors. These localized effects may include, but are not limited to, temperature changes, chemical changes, humidity, and/or changes in physical internal resistance from when first reference calibration has been applied to the device (e.g., that may be specific to the sensor atypical use), to name a few.

For example, as illustrated in FIGS. 4-5, along with the intervals between baseline calibrations varying with respect to the absolute change in set dose, the calibration schedule for a four terminal catalytic type electrochemical sensor can vary for an initial period of time and then become fixed. As shown, along with the intervals between baseline calibrations varying with respect to the absolute change in set dose, the intervals between baseline calibrations in the calibration schedule can initially vary (e.g., 3 hours, 6 hours, 12 hours; 4 hours, 8 hours, 16 hours; etc.) and then become fixed (e.g., 12 hours; 16 hours; etc.).

Figure 7:
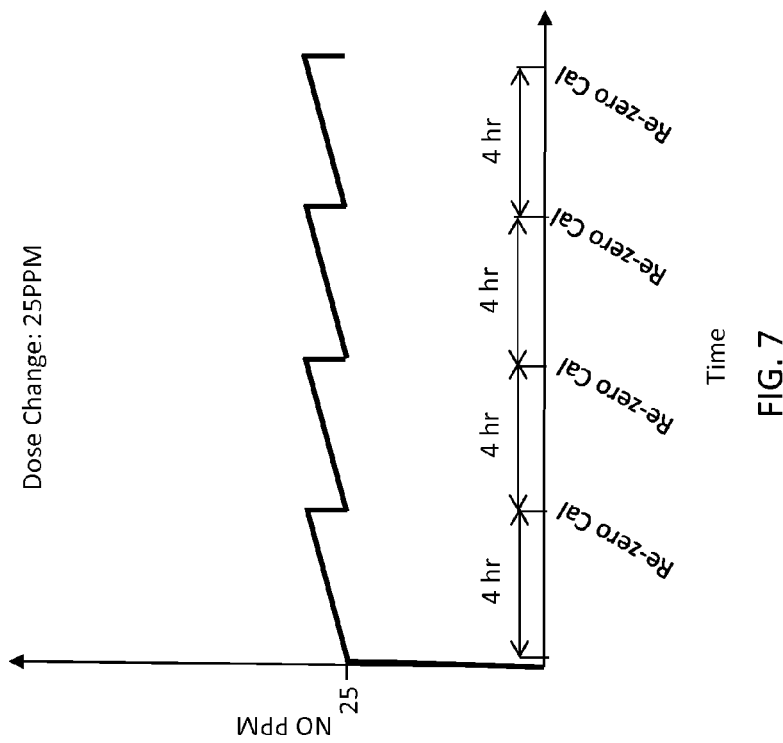
Figure 6:
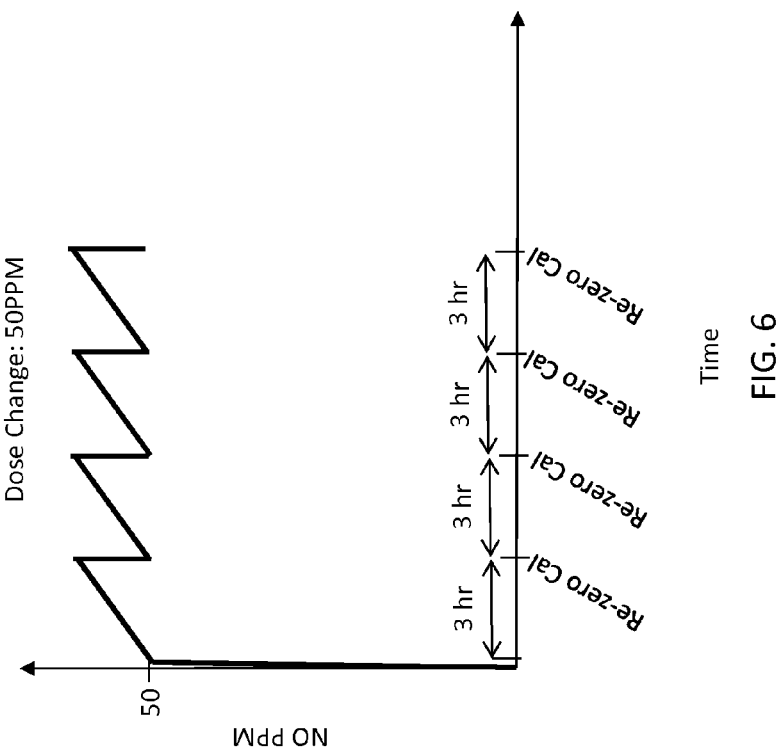

For another example, as illustrated in FIGS. 6-7, along with the intervals between baseline calibrations varying with respect to the absolute change in set dose, the calibration schedule for a three terminal catalytic type electrochemical sensor can be fixed. As shown, along with the intervals between baseline calibrations varying with respect to the absolute change in set dose, the intervals between baseline calibrations in the calibration schedule can be fixed (e.g., 3 hours; 4 hours; etc.).

Figure 9:
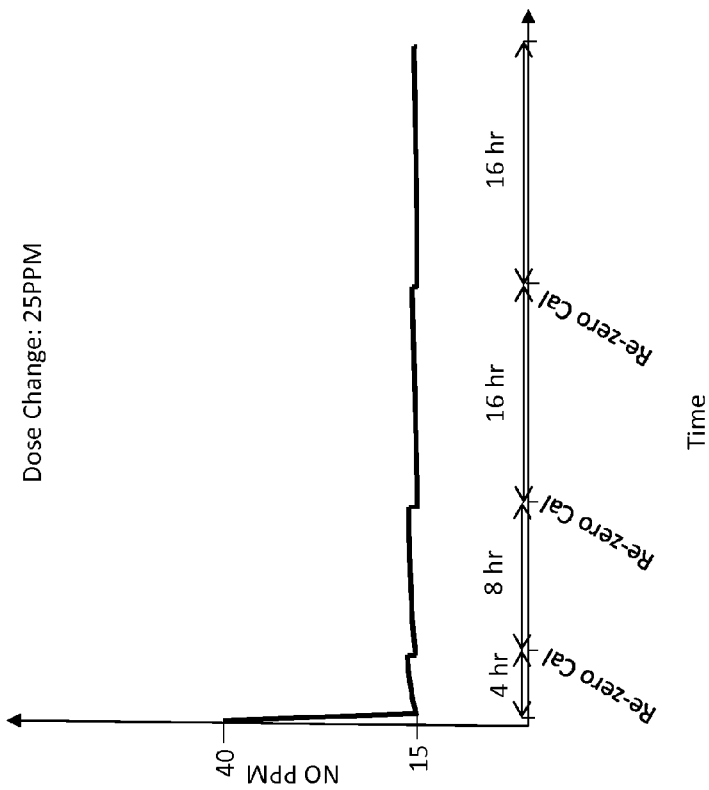
Figure 8:
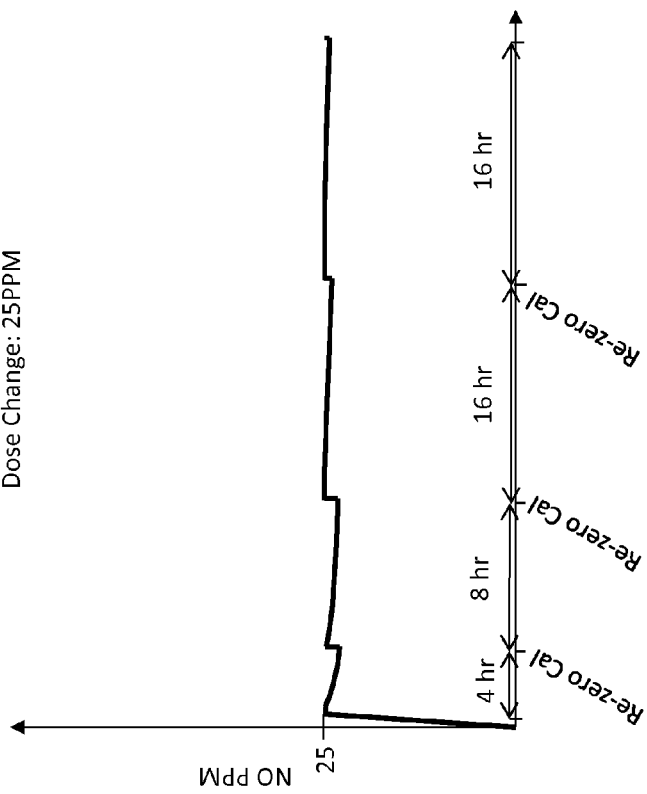

It will be understood that the absolute change in the set dose of NO delivered to the patient refers to the absolute change from zero PPM NO (e.g., prior to delivery of therapeutic NO to the patient) to the initial set dose of NO and changes in the set dose (e.g., changes in the set dose during treatment). In exemplary embodiments, calibration schedules that factor in absolute changes in set dose can treat the absolute change in set dose when first beginning treatment (e.g., initial set dose) the same as changes in the absolute set dose which occur during treatment. For example, the calibration schedule, illustrated in FIG. 8, for a four terminal catalytic type electrochemical sensor having an initial set dose of 25 PPM NO (e.g., a absolute change in set dose of 25 PPM NO) can be the same as the calibration schedule, as illustrated in FIG. 9, for the same four terminal catalytic type electrochemical sensor having an change set dose from 40 PPM NO to 15 PPM NO (e.g., an absolute change in set dose of 25 PPM NO).

In exemplary embodiments, systems and methods of the present invention detect changes in the set dose (e.g., initial set dose, changes in set dose during treatment, etc.), determine the absolute change in set dose, and selected and/or implement the appropriate calibration schedule based on the determined absolute change in set dose. For example, in response to a user setting an initial set dose (e.g., to 50 PPM) the desired auto-calibration schedule for that set dose can be selected, for example, automatically by machine-executable instructions. For another example, in response to a user changing the set dose (e.g., from 75 PPM to 25 PPM; from 25 PPM to 50 PPM; etc.) the desired auto-calibration schedule for that absolute change in the set dose can selected, for example, automatically by machine-executable instructions.

Figure 10:
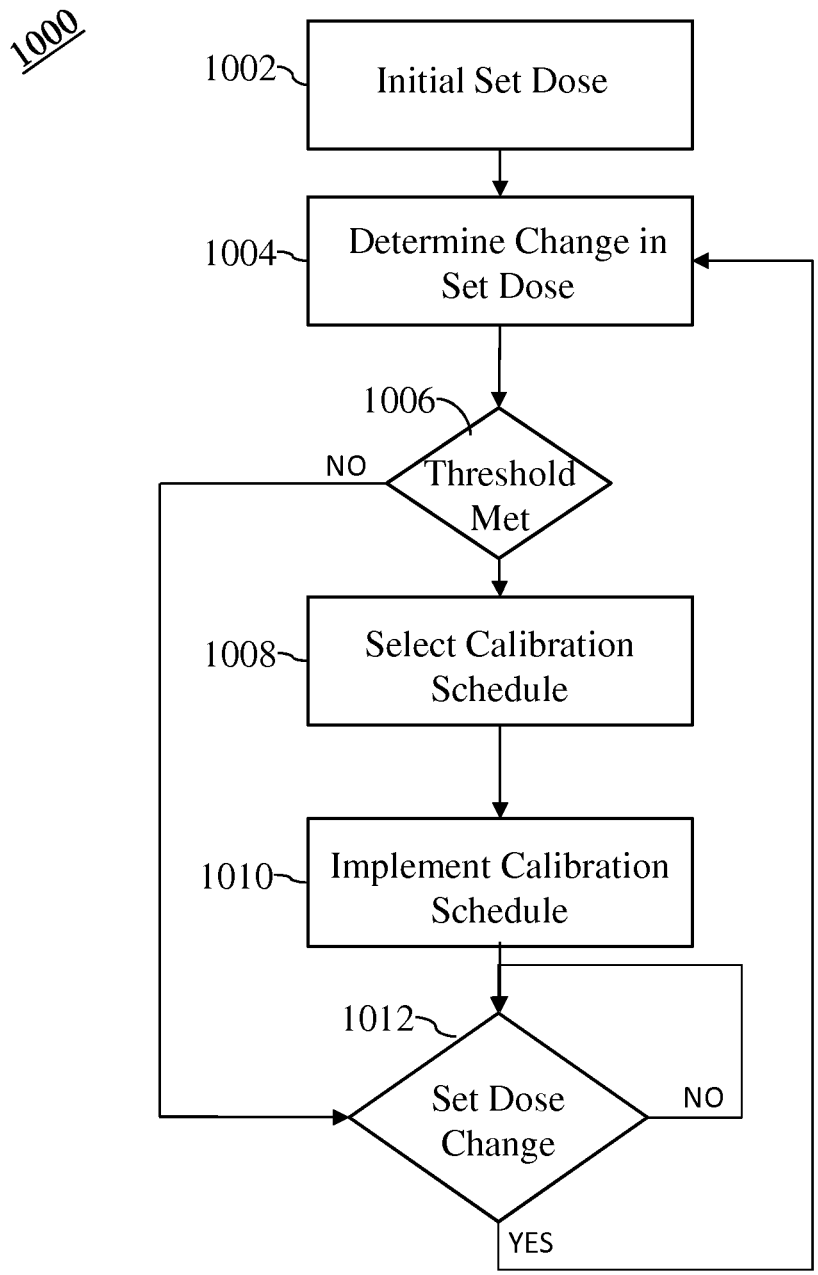
FIG. 10 illustratively depicts an exemplary flowchart for an exemplary set dose change response algorithm for use with exemplary systems for delivering therapeutic nitric oxide gas to a patient, in accordance with exemplary embodiments of the present invention.

Referring to FIG. 10, the therapeutic gas delivery system can perform at least some of the steps in the exemplary method illustrated to, for example, automatically implement the appropriate recalibration schedule in response to a set dose change. Table 1 illustrates and exemplary set of recalibration schedules. By way of example, a set dose change response algorithm 1000 stored in memory (memory affiliated with the therapeutic gas delivery system) can include machine-executable instructions that processors (processors affiliated (operatively associated) with the therapeutic gas delivery system) can access and execute, for example, in response to a change in set dose. This change in set dose can be the initial set dose and/or a change in set dose during delivery of the therapeutic gas to a patient. For ease, the below example distinguishes the initial set dose change from a set dose change during delivery of the therapeutic gas to a patient. This is merely for ease and is in no way meant to be a limitation. One of ordinary skill in the art will recognize that a recalibration schedule can be generated by a formula or an algorithm where applicable.

TABLE 1

| Magnitude of Change in Dose Setting (PPM) | Interval Time Between Calibrations (Hrs) | | | | |
|---|---|---|---|---|---|
| 5 | 24 | 24 | 24 | 24 | 24 |
| 20 | 8 | 12 | 24 | 24 | 24 |
| 25 | 6 | 12 | 24 | 24 | 24 |
| 40 | 4 | 8 | 12 | 24 | 24 |
| 50 | 3 | 6 | 12 | 24 | 24 |
| 80 | 2 | 4 | 8 | 12 | 24 |

At step 1002, an initial set dose can be input (e.g., by the user) and/or an initial set dose value can be stored in memory (memory affiliated with the therapeutic gas delivery system controller). As this is the initial set dose value, at times, the previous set dose value can be presumed to be zero. In some instances, the user may have previously been receiving a set dose, for example, from another therapeutic gas delivery system. For such situations, the user may input (e.g., via the user interface) what the previous set dose (e.g., that was being delivered by another therapeutic gas delivery system to the patient) was and the previous set dose value can be stored in memory (memory affiliated with the therapeutic gas delivery system). Also, for such situations, if applicable, the therapeutic gas delivery system can communicate (e.g., via a communications portal affiliated with the therapeutic gas delivery system) with the other therapeutic gas delivery system (e.g., the previous therapeutic gas delivery system that was delivering therapeutic gas to the patient) and the previous set dose value (e.g., the previous set dose that was being delivered to the patient) can be communicated (e.g., via a communications portal affiliated (operatively associated) with the therapeutic gas delivery system) and stored in memory (memory affiliated with the therapeutic gas delivery system controller).

In exemplary embodiments, an initial auto-calibration may be run to establish an initial baseline, and to compensate for any drift during the time the system may have been off (e.g., during storage, maintenance, change of NO container, etc.). An initial set dose input by a user may then be used to determine the absolute change (i.e., from 0 PPM) and the auto-calibration schedule. In situations where the gas delivery system may be on and running, but have a set dose of 0 PPM, an auto-calibration may be done every 24 hours. During such a period of 0 PPM operation, the sensor may become desaturated, thereby requiring compensation for drift.

In various embodiments, upon boot-up of the therapeutic gas delivery system, the system may immediately initiate a default calibration (e.g., every 24 hours), and begin a baseline calibration after boot-up but before a user may be allowed to enter an initial set dose to ensure that the sensor is calibrated and an accurate baseline value has been stored in the system controller memory. Such initial calibrations may be performed to reset the baseline and/or compensate for desaturation while the device is in storage, or when the therapeutic gas delivery system is powered back on after a previous therapy session, and prior to the next therapy session.

If a user attempts to run a pre-use checkout during such an automatic baseline calibration, the system controller initiating the pre-use checkout can automatically notify the user that they must delay delivery to the patient and monitoring performance tests until the automatic baseline calibration and any re-try attempts are complete.

At step 1004, the therapeutic gas delivery system controller can determine the absolute change in set dose value to, for example, determine if the absolute change in set dose value threshold is met, at step 1006, and/or select a desired calibration schedule, at step 1008. The absolute change in set dose can be determined by calculating the absolute value of previous set dose minus the new set dose. For example, processors (processors affiliated with the therapeutic gas delivery system) can access the previous set dose value (e.g., NO at 50 PPM, NO at 0 PPM, etc.) and subtract the new set dose (e.g., NO at 25 PPM, NO at 40 PPM, etc.) from the previous set dose. This determined absolute change in set dose can be made positive, if needed. In various embodiments, the threshold in set dose may be 5 PPM NO to initiate a determination and/or selection of a recalibration schedule.

At step 1006, the therapeutic gas delivery system controller can determine if a threshold value (e.g., 5 PPM NO) is met to initiate selection and/or implementation of the desired recalibration schedule. This threshold value can be based on a minimum absolute change in set dose and/or a cumulative amount of set dose delivered (e.g., PPM-hours), where the cumulative amount may be 150 PPM hours. A threshold value for initiating selection and/or implementation of the desired calibration schedule may be included in set dose change response algorithm 1000 such that if the absolute change in the set dose and/or cumulative set dose delivery amount is below the threshold then the therapeutic gas delivery system may not select and/or implement a new calibration schedule and/or may store the new set dose value in memory, in the event there is a later change in set dose and/or additional set dose delivered (e.g., to add to the cumulative amount of set dose delivered). Confirmation that the absolute change in set dose is above a threshold (e.g., 5 PPM) may be done as minor changes in set dose and/or minor cumulative amounts of set dose delivered may not necessitate selection and/or implementation of a calibration schedule.

For example, absolute changes in set dose that are less than 5 PPM may not result in substantial drift, therefore a change of 5 PPM or less will not initiate a recalculation or redetermination of a recalibration schedule. For another example, cumulative amounts of set dose delivered that are less than 100 PPM hours (e.g., 20 PPM delivered for 5 hours) this may not result in substantial drift. For yet another example, combined cumulative amounts of set dose delivered that are less than 100 PPM Hours (e.g., 20 PPM delivered for 5 hours) and absolute changes in set dose that are less than 5 PPM may not result in substantial drift. If the threshold is not met, the therapeutic gas delivery system can take no action, and, if a set dose change occurs, proceed to step 1012. If the threshold is met, the therapeutic gas delivery system can proceed to selection and/or implementation of an appropriate calibration schedule.

In exemplary embodiments, at step 1008, processors can then select the appropriate calibration schedule for the determined absolute change in sent dose value, for example, from calibration schedules stored in memory (memory affiliated with the therapeutic gas delivery system) based on the determined absolute change in set dose value.

At step 1010, the therapeutic gas delivery system can implement the selected calibration schedule resulting in baseline calibrations being performed (e.g., automatically) at intervals defined by the selected calibration schedule. For example, when the selected calibration schedule is implemented, the sampling system can perform a method to, for example, execute baseline calibrations comprising: actuating a sampling pump and/or opening a gas sampling valve (e.g., three way valve, etc.) to obtain a gas sample of ambient air (e.g., conditioned room air); expose the gas sample of ambient air to gas sensors (e.g., catalytic electrochemical NO gas sensors) for a period of time; obtain information from the sensor indicative of concentration of target gas (e.g., NO) in the ambient air (e.g., 0 PPM NO); and generate a new calibration and/or modify an existing calibration line by, for example, replacing the initial and/or previous information indicative of zero PPM target gas with the obtained information indicative of zero PPM target gas and using the slope of the initial and/or previous calibration line (e.g., slope of initial and/or previous calibration line connecting the initial and/or previous zero and span calibration points). The calibration line may be stored in the controller memory as a zero intercept value from the baseline calibration and a slope from an initial calibration to provide the values of the formula Y=mx+b, where "m" is the slope and "b" is the zero intercept. The calibration line may be stored in the controller memory as a table of data point values over the calibration span including the zero intercept. Changes in the zero intercept determined by baseline recalibrations may then be used to correct the equation and/or the stored data points, so they represent the new calibration line.

At step 1012, while therapeutic gas delivery system delivers therapeutic gas to the patient, the therapeutic gas delivery system can monitor and/or detect a change in set dose. For example, the therapeutic gas delivery system can detect a change in the value of set dose based on user input changes in the set dose. Of course if no set dose change is detected the therapeutic gas delivery system can continue to check for a set dose change and/or remain waiting to detect a set dose change. If a set dose change is detected, the therapeutic gas delivery system can perform the steps discussed above at step 1004.

Postponing Calibrations

In one or more embodiments, a calibration may be postponed for a period of time if an alarm is active at the time the calibration was intended to take place. The system controller may determine that an alarm is active and continue to recheck the presence of an alarm and/or delay the initiation of a calibration operation for a set interval (e.g., that may begin after the alarm clears) and recheck for the alarm after the set interval has expired. In embodiments, the system controller may monitor the alarm and determine when the alarm has been cleared, at which time the controller may delay an auto-calibration by a predetermined time, for example, to ensure the alarm is not retriggered. In addition, the system controller may determine if an alarm was previously activated within a predetermined time period before the calibration is to be executed, wherein the calibration may be postponed if the active alarm is detected and executed if the active alarm is not detected. The controller may also monitor the occurrence of other activities and/or off-line circumstance that may otherwise interfere with auto-calibration and institute a delay to allow such circumstance to be resolved. The system controller may also detect if a user is interacting or has interacted with the therapeutic gas delivery system within a predetermined timeframe at the time the calibration is to be executed, wherein the calibration is postponed if the user is interacting or has interacted with the therapeutic gas delivery system within the predetermined timeframe, and executed if the user is not interacting or has not interacted with the therapeutic gas delivery system within the predetermined timeframe.

In one or more embodiments, a calibration may be postponed for a period of time if the user is interacting with therapeutic gas delivery system at the time the calibration was intended to take place. Interactions can include, but is not limited to, interaction with the user input, changing of the therapeutic gas source, changing the gas sample conditioner, decoupling the delivery system from a cart affiliated with it, purging, etc. The system controller may determine that the user is interacting with the delivery system and continue to recheck the presence of an alarm and/or delay the initiation of a calibration operation for a set interval (e.g., after the last interaction ends) and recheck for user interaction after the set interval has expired.

In one or more embodiments, a calibration may be postponed for a period of time if the sensor output during a baseline recalibration with ambient air indicates the presence of an interfering gas, for example $H_2S$, $NO_2$, etc. interfering gas that may come from cleaning products, flatulence, a leak in the system, or other contaminant sources. In such instances, the recalibration will be interrupted and/or rejected and rescheduled for a time 1, 5, 10, or 15 minutes later to allow the ambient air to clear. In at least some instances, postponing a calibration may be required because the new baseline calibration based on the sensor output during this period of time would not be necessarily be indicative of the sensors drift and this can lead to the new calibration line being inaccurate. This can lead to improper dosing information being displayed to the user. In at least some instances, this sensor output is rejected ensuring that it is not used for compensation of drift. In various embodiments, the system controller may detect if one or more interfering gasses are causing or have caused sensor output to be outside a threshold range within a predetermined timeframe at the time the calibration is to be executed, wherein the calibration is postponed if the sensor output is or has been out of range within the predetermined timeframe at the time the calibration is to be executed, and executed if the sensor output is not or has not out of range within a predetermined timeframe. In various embodiments, the system controller may detect if one or more interfering gasses are causing or have caused a postponement of a calibration due to detection of sensor output outside a threshold range within a predetermined timeframe at the time the calibration is to be executed, wherein the calibration may be postponed again if the sensor output is still out of range within the predetermined timeframe at the time the calibration is to be executed, and executed if the sensor output is not out of range within a predetermined timeframe.

In exemplary embodiments, the system controller can determine when an interfering gas may be effecting the sensor because the sensor output may be outside of the range expected due to drift (e.g., 0 ADC counts to 655 ADC counts). For example, the system controller can postpone a calibration when the sensor output is greater than an expected output threshold. In at least some embodiments, the expected output threshold can be 0 ADC counts to 655 ADC counts and when the sensor output is outside this expected output threshold the system controller can postpone the calibration a period of time (e.g., 1, 5, 10, or 15 minutes). The sensor can then undergo the calibration; however, if the sensor output is again above the expected output threshold the calibration can again be postponed. This can be repeated as needed thereby ensuring that the interfering gas has dispersed (e.g., allowing the ambient air to clear).

Calibration Schedules (Quantity)

In exemplary embodiments, there may only be one or a small number of calibration schedules stored in memory (memory affiliated with the therapeutic gas delivery system). A limited number of calibration schedules may be available for selection to, for example, conserve on memory usage and/or reduce complexity. For example, in at least some exemplary embodiments, only one calibration schedule may be stored in memory and/or this calibration schedule may be selected to address the largest absolute change in set dose seen under the vast majority of uses. Using this calibration schedule for this set dose (e.g., that is the largest seen the vast majority of the time) then at step 1008 only this schedule may be available for selection. This can be beneficial as memory usage and/or complexity can be reduced, while a calibration schedule can be implemented that addresses sensor drift while also reducing the quantity and/or duration of times the sensor goes offline. By way of example, as the vast majority (e.g., 99%, etc.) of all deliveries of therapeutic gas may be less than a set dose of NO at about 50 PPM, then using a calibration schedule based on an absolute change in set dose of 50 PPM addresses the worst case scenario as well as provides the benefit of reduced sensor time offline. Following this example, if the absolute set dose change is, for example, 20 PPM the calibration schedule used may be that for an absolute set dose change of 50 PPM.

Sample Valve

In exemplary embodiments, the above described gas sampling valve (e.g., valve(s) 118 illustrated in FIGS. 1A-1B) can be a three way valve in fluid communication with the gas sensors (e.g., NO sensor); the gas in the breathing circuit (e.g., via sampling line 124 illustrated in FIG. 1); and calibration gas such as ambient air, that may be conditioned, (e.g., via sampling line 134 illustrated in FIG. 1). Using a three way valve, when the valve is opened in a first position the sensors can be exposed to samples of gas in the breathing circuit, while calibration gas flow is restricted and when the valve is opened in a second position the sensors can be exposed to calibration gas (e.g., ambient conditioned air), while sample gas flow from the breathing circuit is restricted. Utilizing the above configuration, when a baseline calibrations are being performed the breathing circuit sample line does not need to be disconnected from the breathing circuit and/or the therapeutic delivery system. Without such configuration users may be required to disconnect the breathing circuit sample line from the breathing circuit and/or the therapeutic delivery system, which can be undesirable as, generally speaking, modification to the breathing circuit can increase risk of damaging the circuit or components affiliated with it, increase risk to the patient, and/or impact delivery of therapeutic gas to the patient.

In at least some instances, systems and methods of the present invention can detect whether the gas sampling valve is functioning properly to, for example, prevent improper calibration. This can be particularly important for baseline calibrations performed automatically as the user may not be present to observe the gas sensor readings during calibration. In exemplary embodiments, the therapeutic gas delivery system can detect whether the gas sampling valve is functioning properly by monitoring the electrical current the sampling valve uses (e.g., current pulled when actuated, etc.) and/or by monitoring the flow and/or pressure in the sampling lines (e.g., sampling line 134 and/or sampling line 124 illustrated in FIGS. 1A-1B, etc.). For example, the therapeutic gas delivery system can detect whether the gas sampling valve is functioning properly by monitoring the pressure and/or flow in the gas sample line just upstream of the sample pump as the pressure and/or flow in the line for receiving ambient and/or span samples (e.g., sample line 134 illustrated in FIG. 1A) may be different than the pressure and/or flow in the line for receiving samples from the patient breathing circuit (e.g., sample line 124 illustrated in FIG. 1A). In various embodiments, the ADC counts just prior to a calibration may be stored in temporary memory for comparison with the ADC counts during the baseline calibration, where an insignificant change in the ADC counts may indicate that the valve has not functioned properly. When detected as not functioning properly the calibration can be postponed, retried, and/or may be cancelled.

User Notification

In exemplary embodiments, the display may be blank during a calibration to avoid a user misinterpreting such values during a calibration as a set dose reading. To avoid such confusion, a message indicating that a calibration is in effect may be displayed to a user and/or recorded in the electronic medical record (EMR) to inform a user of the system's activity. For example, the user can be informed that the concentration monitoring of the inspiratory line 127 of breathing circuit 126 is presently off-line, for example by a suitable message and/or auditory indicator.

In exemplary embodiments, alarms for the system may be taken off-line to avoid triggering an alarm due to the discrepancy between the set dose and the concentration be measured by the sensor during the calibration. This may be referred to as an alarm blackout. This alarm blackout may also cause confusion for a user that expects an alarm when the measured concentration (e.g., displayed to the user) differs from the set dose. A message that the alarm(s) have been disabled during the calibration period (e.g., 5 to 10 minutes) may be displayed, so the user is properly informed.

In exemplary embodiments, the system may alert the user that a calibration has failed. This may occur if the valve does not function properly, or multiple attempts at calibration produce sensor values that are outside the threshold values, the number of calibration retries (e.g., 4, 5, 6, etc.) before a failure message is displayed may be selected by a user or predetermined and hard-coded into the system controller or stored in memory.

Drift Overview

As mentioned above, while not intending to be bound by theory, or to limit the scope of the invention in any way, it is presently believed that although the auxiliary electrode and sensing electrode are intended to be under nearly identical conditions with the exception that the sensing electrode is exposed to the target gas (e.g., NO) while the auxiliary electrode is not exposed to the target gas, there appears to be localized effects which may cause the auxiliary electrode and sensing electrode not, at least for an initial period of time, to be under identical conditions. These localized effects may include, but are not limited to, temperature changes, chemical changes, humidity, and/or changes in physical internal resistance from when first reference calibration has been applied to the device (e.g., that may be specific to the sensor atypical use), to name a few.

Regarding chemical effects, it is believed that the electrolyte in the catalytic type electrochemical gas sensor (e.g., NO sensor) may be polluted by oxides (e.g., oxides of the Nitrogen from the NO), for example, because the concentration of NO used can be substantially higher than the concentration that these types of sensors may be exposed to conventionally and/or because the duration of exposure of these sensors when used in therapeutic NO delivery can be substantially longer than the exposure duration these sensors may have when used conventionally for toxic gas emission measurements. In at least some instances, it is believed that this localized effect may be the cause, dominant cause, for sensor drift seen when using the sensor atypically.

Regarding temperature effects, referring back to FIG. 2A, it has been found that the baseline signal of three terminal electrochemical sensors used under continuous duty tends to increase exponentially with time and temperature (e.g., approximately doubling for every 30° C. rise in temperature). This percentage signal change related to temperature change has been found to be similar between the baseline signal output and for a given target concentration. In electrochemical sensors that include an auxiliary electrode (e.g., four terminal electrochemical sensors), auxiliary electrode 218 can be located in close proximity to sensing electrode 202 without being exposed to the reactive gas so auxiliary electrode 218 and sensing electrode 202 can be at the same temperature. With the auxiliary electrode 218 and the sensing electrode 202 at the same temperature (and with auxiliary electrode 218 not being exposed to the target gas while sensing electrode 202 is exposed to the target gas) the signal from auxiliary electrode 218 can be subtracted from sensing electrode 202 to compensate for long term drift caused by temperature effects. Although the above technique can be used for some scenarios (e.g., for conventional uses of these sensors), it has been determined that for inhaled NO therapy such techniques may not sufficiently correct for baseline drift.

After extensive research, it was found that when these catalytic type electrochemical sensors (e.g., sensors that are suitable for use with low concentrations of NO or for short periods of time) are used atypically for inhaled NO therapy, drift may be associated with auxiliary electrode 218 drifting at a differing rate than sensing electrode 202; temperature changes local to the sensing electrode 202 not being detected by auxiliary electrode 218; and/or auxiliary electrode 218 heating up at a differing rate than sensing electrode 202.

It was also found that these temperature changes may be caused and/or exacerbated by the target gas (NO) having an exothermic (or endothermic) reaction at one or more of the electrodes (e.g., sensing electrode 202, counter electrode 206, etc.). In some instances, although these temperature changes may not be substantial when using these sensors in a conventional manner, these temperature changes may be substantial for the atypical use of these sensors for inhaled NO therapy, for example, because the concentration of NO used can be substantially higher than the concentration that these types of sensors may be exposed to conventionally and/or because the duration of exposure of these sensors when used in therapeutic NO delivery can be substantially longer than the exposure duration these sensors may have when used conventionally for toxic gas emission measurements.

Noting the above, local changes in temperature at sensing electrode 202 may not be detected, or may be detected at a different rate, at the auxiliary electrode 218. With this local temperature change at sensing electrode 202 not also occurring at auxiliary electrode 218, cell "base current" drift may not be corrected, as described above, by simply subtracting the signal from auxiliary electrode 218 from sensing electrode 202. Further research also found that if the reactive gas is supplied (e.g., at the same concentration) for a long enough duration of time (e.g., 24 hours) then the temperature at auxiliary electrode 218 may eventually be the same as the temperature at sensing electrode 202, for example, because electrochemical sensor 200 may eventually obtain steady state, equilibrium, or the like.

Temperature Compensation

In exemplary embodiments, rather than and/or in combination with the above calibration processes, to address at least some of the above described surprising phenomena, the local temperature at the sensing electrode (e.g., at specific times due to a set concentration of NO being sensed) can be estimated (e.g., mathematically, using heat transfer analysis, etc.). Further, the known signal (e.g., determined empirically) typically generated by the auxiliary electrode 218 at that estimated temperature can then be subtracted from the signal generated by the sensing electrode. Using this technique baseline drift local to the sensing electrode can be compensated for at specific times. After steady state has been achieved baseline drift related to temperature can be compensated, as described above, by simply subtracting the signal from auxiliary electrode 218 from sensing electrode 202.

By way of example, to determine the local temperature at the sensing electrode and/or the distribution of heat (or variation in temperature) in electrochemical sensor 200 over time the heat equation can be used. This distribution of heat with respect to time can then be compensated for, for example, by subtracting the signal that would be expected to come from auxiliary electrode 218 if it were at the same temperature as sensing electrode 202 from sensing electrode 202.

By way of another example, the local temperature at sensing electrode 202 at various times can be determined and/or compensated for using other methods. For example, a lumped capacitance model can be used. For another example, empirical knowledge can be used.

In exemplary embodiments, to address at least some of the above described phenomena, the electrochemical sensor 200 can be cooled. This cooling may need to be substantial enough so that if an exothermic reaction is occurring that heat generated may effectively be dominated by the cooling temperature. Alternatively, this cooling may need to be substantial enough so the steady state temperature of electrochemical sensor 200 may effectively be dominated by the cooling temperature.

In exemplary embodiments, to address at least some of the above described phenomena, the steady state temperature of electrochemical sensor 200 and/or the local temperature of the sensing electrode (e.g., when the steady state is reached) can be determined (e.g., mathematically, empirically, etc.) and then electrochemical sensor 200 can be pre-heated to that temperature or near that temperature, for example, to reduce the time needed for electrochemical sensor 200 to reach steady state. By way of example, the electrochemical sensor can be preheated to a known temperature of the sensing electrode for a known concentration and then that when that known concentration is added the heat source can be decreased back to the steady state of the electrochemical sensor (e.g., not the local temperature at the sensing electrode).

In exemplary embodiments, to address at least some of the above described phenomena, a secondary sensing electrode (in the same sensor or in a different sensor used in the same NO delivery stream) may be intermittently turned on to provide the appropriate signal output for the concentration being delivered. The difference between the signal output of the sensing electrode and the signal output of this secondary sensing electrode can then be removed (e.g., as it would be related to drift related to temperature) to compensate for zero drift. The frequency of the secondary sensing electrode being used can be adjusted with respect to time. It will be understood that the sensor used (e.g., primary electrochemical sensor having a primary sensing electrode, secondary electrochemical sensor providing a secondary sensing electrode, etc.) may be a three terminal (e.g., no auxiliary electrode).

Dual NO Sensors

In exemplary embodiments, the therapeutic gas delivery system can include two or more catalytic type electrochemical sensors (e.g., two or more NO sensors) wherein when one of the sensors is undergoing a calibration (e.g., baseline calibration, etc.) the other sensor is exposed to sample gas from the breathing circuit. Using this technique, when one sensor is offline (e.g., undergoing calibrations, undergoing baseline calibrations, etc.) the other sensor can be online. Hence, the user sees no offline period during calibrations and can be provided, without interruption, for example, in the user interface, with confirmation that the concentration of therapeutic gas the patient is receiving is the desired set dose. In exemplary embodiments, the sensors can intermittently monitor (e.g., one sensor can be exposed to sample gas while the other sensor is exposed to zero concentration gas) such that neither sensor saturates. In exemplary embodiments, the second sensor can be used for determination of drift on the same schedule as zeroing.

In contrast to using two sensors to continuously monitor a sample gas, intermittent monitoring reduces the rate at which the sensors age and increases the amount of time before sensor failure. Continuous exposure of a sensor to low humidity gas can cause the sensor electrolyte to dry out. Using one sensor as a first or primary sensor and a second sensor as a backup sensor results in the sensors being under different conditions for different lengths of time. In addition, whereas continuous exposure of both sensors can result in increasing drift of both sensors at a comparable rate, which can cause cross-checking to be inaccurate, and may lead to near simultaneous failure of both sensors, intermittent exposure of the backup sensor to the sampler gas in the inspiratory line during calibrations increases the sensors lifespan and allows a cross-check of the primary sensor by a backup sensor with reduced drift. Intermittent use of the backup sensor also avoids saturation of the sensor with the target gas. Cross-checking allows two sensors to provide two separate calibration values that can be compared to determine whether the relative amount of drift is greater than a threshold value. If both sensors have similar but excessive drift due to equivalent exposures and aging, the cross-check would give the impression of less drift than actual.

Sample Gas (Concentration Reduction)

In exemplary embodiments, prior to exposing the catalytic type electrochemical sensor (e.g., NO sensor) to sample gas from a breathing circuit that may contain substantially high concentrations (e.g., >5 PPM) of target gas (e.g., NO), the sample gas can be stream blended down (also known as ratio-metric) so the concentration of target gas (e.g., NO) is reduced by a known amount. The output from the sensor can then factor in the known amount the target gas has been diluted to provide the user with confirmation that the therapeutic gas (e.g., NO) is being delivered at the desired concentration (e.g., desired set dose). By reducing the concentration of target gas (e.g., NO) that the sensor (e.g., NO sensor) is exposed to, drift may be reduced and/or eliminated while still enabling monitoring of the set dose being delivered to the patient.

By way of example, diluent gas flow (e.g., from a source of non-reactive gas, nitrogen gas flow, etc.) can be stream blended proportional to sample gas flow from the breathing circuit to reduce the concentration of NO in the sample gas. Sample gas flow can be known, for example, as the sample pump may pull sample gas at a known flow rate, the flow rate of the gas can be controlled, for example, by a valve(s), and/or sample gas flow sensors can measure the flow of sample gas flow. Diluent gas flow (e.g., from a source of non-reactive gas, nitrogen gas flow, etc.) can be known, for example, as it may be provided by and/or pulled by a pump; a flow sensor may be used to measure gas flow; and/or the flow rate of the gas can be controlled, for example, by a valve(s).

In exemplary embodiments, the therapeutic gas delivery system can execute, for example, using machine-executable instructions, a sample gas concentration reduction calculation to blend the sample gas with a diluent gas using diluent gas at known concentration such as nitrogen (e.g., from a nitrogen gas tank); the amount of sample gas flow from the patient circuit using a sample gas flow sensor and/or the known flow of a sample pump; and the amount of diluent gas flow reported by a gas flow sensor, the known flow of diluent gas from a diluent gas pump, and/or the known flow of diluent gas from a flow controller such that the final NO concentration at the NO sensor would be a fraction concentration delivered to the patient. Reducing the average concentration will minimize long term drift. (e.g., valve(s), etc.).

Intermittent Monitoring

In exemplary embodiments, to at least reduce drift of the catalytic type electrochemical gas sensor (e.g., NO sensor), the concentration of therapeutic gas (e.g., set dose of NO) being delivered to the patient may be monitored intermittently, where the gas sensor is exposed to the target gas for a limited period of time rather than continuously. In various embodiments, the exposure time may be slightly greater than the response time of the sensor. By intermittently monitoring (e.g., rather than constantly monitoring) the target gas concentration the amount of time that the sensor is exposed to the target gas can be reduced, and during times of non-exposure to the target gas, the sensor can be exposed to ambient air (e.g., conditioned ambient air). This can be accomplished using catalytic type electrochemical gas sensors (e.g., NO sensors) which have a substantially fast response time (e.g., a few seconds, less than five seconds, etc.).

By way of example, rather than using a catalytic type electrochemical sensor (e.g., NO sensor) with a response time of about 15 seconds, catalytic type sensors with a response time of about 5 seconds may be used, where the sensor may be exposed to the target gas (e.g., high concentration NO) for 5 seconds and exposed to ambient air (e.g., conditioned ambient air) for 10 seconds and/or for at least some of the remaining 10 seconds. During the period of non-exposure to the target gas, the output displayed to users by the user interface may be the value measured during the period of exposure. Using this technique sensor drift can be reduced and/or eliminated, while also providing users with effectively the same desired information (e.g., confirmation that the desired set dose is being delivered).

Those skilled in the art will readily recognize numerous adaptations and modifications which can be made to the therapeutic gas delivery systems and method of delivering a pharmaceutical gas of the present invention which will result in an improved method and system for introducing a known desired quantity of a pharmaceutical gas into a patient, yet all of which will fall within the scope and spirit of the present invention as defined in the following claims. Accordingly, the invention is to be limited only by the following claims and their equivalents.

Reference throughout this specification to "one embodiment," "certain embodiments," "one or more embodiments," "exemplary embodiment," "exemplary embodiments," and/or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment," "exemplary embodiment," "exemplary embodiments," and/or "in an embodiment" in various places throughout this specification are not necessarily referring to the same embodiment of the invention. Furthermore, the particular features, structures, materials, or characteristics can be combined in any suitable manner in one or more embodiments.

It will be understood that any of the steps described can be rearranged, separated, and/or combined without deviated from the scope of the invention. For ease, steps are, at times, presented sequentially. This is merely for ease and is in no way meant to be a limitation. Further, it will be understood that any of the elements and/or embodiments of the invention described can be rearranged, separated, and/or combined without deviated from the scope of the invention. For ease, various elements are described, at times, separately. This is merely for ease and is in no way meant to be a limitation. It will be understood that, at times, headings may be used. This is merely for ease and is in no way meant to be a limitation.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

The invention claimed is:

1. A method for compensating nitric oxide sensor drift affiliated with nitric oxide delivery, comprising:
storing, in a non-transitory computer-readable memory affiliated with a nitric oxide delivery system, a calibration line correlating expected output values from a nitric oxide sensor to nitric oxide concentrations and a calibration schedule providing times for performing a plurality of baseline calibrations, the baseline calibrations being performed in response to a set dose change, the baseline calibrations including exposing the nitric oxide sensor to a zero concentration of nitric oxide;
supplying, via the nitric oxide delivery system, nitric oxide into an inspiratory flow of a patient breathing circuit, according to a set dosage;
monitoring output values from the nitric oxide sensor, the nitric oxide sensor in fluid communication with the breathing circuit, the output values indicative of the therapeutic gas concentration in the inspiratory flow;
determining the actual output value of the nitric oxide sensor during a baseline calibration of the nitric oxide sensor in accordance with the calibration schedule; and
augmenting the expected values correlated to nitric oxide concentrations to include the difference in the actual output value and the expected output value.

2. The method of claim 1 wherein the calibration schedule includes a set of values representing intended intervals between calibrations.

3. The method of claim 1 further comprising the step of postponing the baseline calibration when there is an alarm condition.

4. The method of claim 1 further comprising the step of postponing the baseline calibration when an alarm condition occurs within a predetermined interval before the time the baseline calibration is scheduled to occur.

5. The method of claim 1 further comprising the step of postponing the baseline calibration when the presence of an interfering gas is detected.

6. The method of claim 1 wherein the baseline calibration includes exposing the nitric oxide sensor to ambient air.

7. A method for compensating nitric oxide sensor drift affiliated with nitric oxide delivery, comprising:
storing a calibration schedule and a calibration line in a non-transitory computer-readable memory of a system controller, the calibration schedule providing zero concentration nitric oxide sensor calibrations in response to a change in set dose, and the calibration line providing output values from a nitric oxide sensor correlated to nitric oxide concentrations;
supplying, via a nitric oxide delivery system, nitric oxide to a patient breathing circuit according to a set dosage;
continuously monitoring output values from the nitric oxide sensor affiliated with the nitric oxide delivery system that are correlated to the concentration of nitric oxide in the breathing circuit;
identifying that a nitric oxide sensor calibration should be performed according to the calibration schedule;
exposing the nitric oxide sensor to a flow of a gas having a zero concentration of nitric oxide;
measuring the concentration of nitric oxide detected by the nitric oxide sensor during exposure to the gas having a zero concentration of nitric oxide; and
adjusting the calibration line according to a detected drift between a baseline and the concentration of nitric oxide measured when the nitric oxide sensor is exposed to the gas having a zero concentration of nitric oxide.

8. The method of claim 7 wherein the nitric oxide sensor is exposed to the gas having a zero concentration of nitric oxide for a predetermined interval before the calibration line is adjusted.

9. The method of claim 7 wherein the gas having a zero concentration of nitric oxide is ambient air.

10. The method of claim 7 further comprising the step of postponing the calibration when there is an alarm condition.

11. The method of claim 7 further comprising the step of postponing calibration when an alarm condition occurs within a predetermined interval before the scheduled calibration.

12. The method of claim 7 further comprising the step of postponing the calibration when the presence of an interfering gas is detected.

13. A method for calibrating for nitric oxide sensor drift in a nitric oxide delivery system, comprising:
   storing a calibration schedule and a calibration line in a non-transitory computer-readable memory of a system controller;
   wherein the calibration line has a baseline associated with a zero concentration of nitric oxide;
   receiving via the system controller a set dosage of nitric oxide;
   delivering nitric oxide to a breathing circuit according to the set dosage;
   continuously collecting via a nitric oxide sensor measurements of the concentration of nitric oxide in the breathing circuit;
   adjusting the measurements of the concentration of nitric oxide in the breathing circuit according to the calibration line and presenting a representation of the adjusted measurements on a display;
   identifying that a calibration should be performed according to the calibration schedule;
   performing a calibration, including:
   exposing the nitric oxide sensor to a gas having a zero concentration of nitric oxide for a predetermined interval,
   measuring the concentration of nitric oxide detected by the nitric oxide sensor while it is exposed to the gas having a zero concentration of nitric oxide, and
   adjusting the calibration line according to the difference between the baseline and the measured concentration of nitric oxide measured when the nitric oxide sensor is exposed to the gas having a zero concentration of nitric oxide; and
   resuming the continuous collecting of measurements of the concentration of nitric oxide in the breathing circuit.

14. The method of claim 13 wherein the baseline is associated with the nitric oxide concentration detected during a previous calibration.

15. The method of claim 13 wherein the gas having a zero concentration of nitric oxide is ambient air.

16. The method of claim 13 further comprising the step of postponing the calibration when there is an alarm condition.

17. The method of claim 13 further comprising the step of postponing the calibration when an alarm condition occurs within a predetermined interval before the scheduled calibration.

18. The method of claim 13 further comprising the step of postponing the calibration when the presence of an interfering gas is detected.

19. The method of claim 13 wherein the calibration schedule includes a set of values representing intended intervals between calibrations.

20. The method of claim 13 further comprising the step of postponing the calibration when there is an alarm condition.

* * * * *